United States Patent [19]
de Bont et al.

[11] Patent Number: 5,760,072
[45] Date of Patent: Jun. 2, 1998

[54] PACLITAXEL PRODRUGS, METHOD FOR PREPARATION AS WELL AS THEIR USE IN SELECTIVE CHEMOTHERAPY

[75] Inventors: Hendricus B. A. de Bont; Ruben G. G. Leenders, both of Nijmegen; Johan W. Scheeren, Malden; Hidde J. Haisma, Hoevelaken; Dick de Vos, Oegstgeest, all of Netherlands

[73] Assignee: Pharmachemie B.V., Haarlem, Netherlands

[21] Appl. No.: 722,941

[22] Filed: Sep. 30, 1996

[30] Foreign Application Priority Data

Dec. 29, 1995 [EP] European Pat. Off. ............ 95203671

[51] Int. Cl.$^6$ .................... A61K 31/335; C07D 305/14
[52] U.S. Cl. ..................... 514/449; 549/414; 549/510; 549/511
[58] Field of Search ............... 514/449; 549/510, 549/511, 414

[56] References Cited

FOREIGN PATENT DOCUMENTS

89/08453  9/1989  WIPO.

OTHER PUBLICATIONS

R.G.G. Leenders et al. "beta–Glucuronyl Carbamate Based Pro–moieties Designed for Prodrugs in ADEPT", Tetrahedron Letters, vol. 36, No. 10, pp. 1701–1704, Mar. 1995, Oxford GB.

K.C. Nicolaou et al, "Design, Synthesis and Biological Activity of Protaxols", Nature, vol. 364, No. 6436, Jul. 29, 1993, p. 464–466.

Y. Ueda et al, Synthesis and Antitumour Evaluation of 2'-Oxycarbonylpaclitaxels (Paclitaxel-2'-Carbonates), Bioorganic and Medicinal Chemistry Letters, vol. 4, No. 15, 1994, pp. 1861–1864.

M.L. Rodrigues et al, "Synthesis and beta–lactamase–mediated Activation of a Cephalosporin–taxol Prodrug", Chemistry and Biology, vol. 2, April 1995, pp. 223–227.

*Primary Examiner*—Ba K. Trinh
*Attorney, Agent, or Firm*—Browdy and Neimark

[57] ABSTRACT

A paclitaxel prodrug has a paclitaxel portion coupled to a cleavable N-(aliphatic or aromatic)-O-glycosyl carbamate spacer group, and can be administered orally, topically or by injection to provide an anti-tumor effect, the prodrug being activated by a hydrolizing enzyme, an endogeneous enzyme or an exogeneous enzyme.

5 Claims, No Drawings

PACLITAXEL PRODRUGS, METHOD FOR PREPARATION AS WELL AS THEIR USE IN SELECTIVE CHEMOTHERAPY

This invention relates to novel paclitaxel prodrugs, their synthesis and use alone or in combination with enzymes, or antibody enzyme conjugates.

More specifically, this invention relates to novel, water-soluble paclitaxel prodrugs wherein paclitaxel is coupled to an enzymatically cleavable N-(aliphatic or aromatic)-O-glycosyl carbamate spacer group, and having formulae 1 or 2a, b:

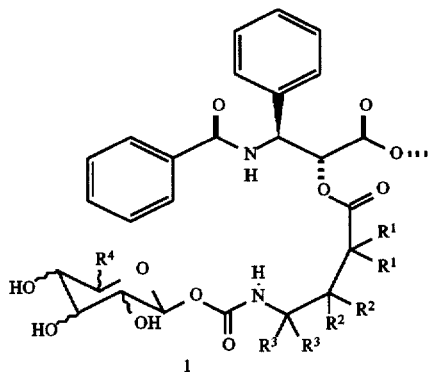

1

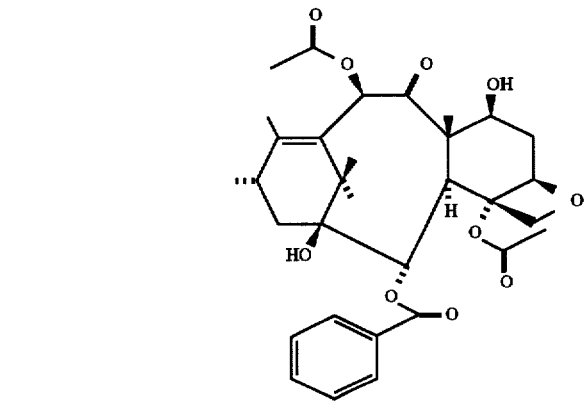

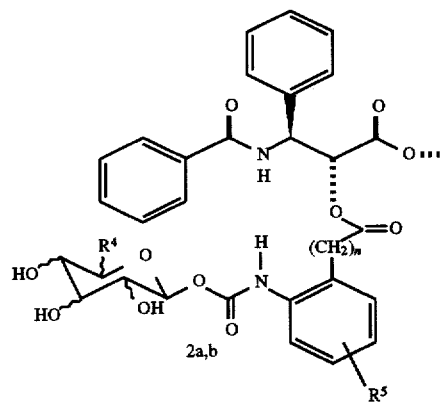

2a,b

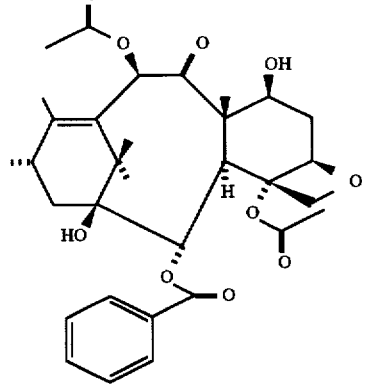

-continued wherein
$R^1$, $R^2$, $R^3$ = —H or —$CH_3$
$R^4$ = —$CH_2OH$, —$C(O)O^-Z^+$
$R^5$ = —H, —$CX_3$, —OY, —NHY, —$S(O)_2Y$, —$C(O)Y$, —$C(O)OY$
X = halogen
Y = $C_1$-$C_3$ alkyl, aryl
Z = H, Li, Na, K
n = 1(a) or 2(b).

as well as the acid addition, salts thereof.

Paclitaxel is thus through its 2'-hydroxyl functionality connected to a, cleavable spacer group, which is in turn attached to a preferably enzymatically cleavable sugar group.

The lack of selectivity of cytostatic agents for tumor cells is a serious drawback in conventional cancer chemotherapy. New methods to increase the selectivity of anti-cancer agents are under study and the use of monoclonal antibodies ($M_{ab}$) to target cytotoxicity to tumor cells is one of them. In this context relatively non-toxic prodrugs can be used in cancer treatment which are selectively activated at the tumor site by the action of endogenous enzymes or targeted enzymes, or via a non-enzymatic process.

The invention therefore also relates to the use of a paclitaxel prodrug having formulae 1 or 2a,b, wherein $R^1$, $R^2$, $R^3$, $R^4$, $R^5$, X, Y, Z and n are defined as above, in the preparation of a medicament for use in a target tissue treatment, wherein the prodrug is activated by hydrolysis. Preferably said hydrolysis is effected by means of an enzyme.

ADEPT (Antibody Directed Enzyme Prodrug Therapy) is a therapy in which an antibody targets an enzyme to the tumor site. After the enzyme has been situated at the tumor, the relatively non-toxic prodrug 1 or 2a,b is given which is converted to the parent drug by action of the appropriate enzyme.

Another possibility is the activation of the prodrugs 1 or 2a,b by endogenous enzymes or by a specific hydrolysis resulting in liberation of the parent drug. Prodrugs having general formula 1 and 2a,b can be converted to paclitaxel (3) by the action of certain glucuronidases or glycosidases conjugated to i.e. monoclonal antibodies or immunoliposomes (see for example M. H. Vingerhoeds et al. FEBS 1993, 336, 485–490), or by the action of catalytic antibodies (see for example H. Miyashita et al. Proc. Natl. Acad. Sci. USA 1993, 90, 5337–5340).

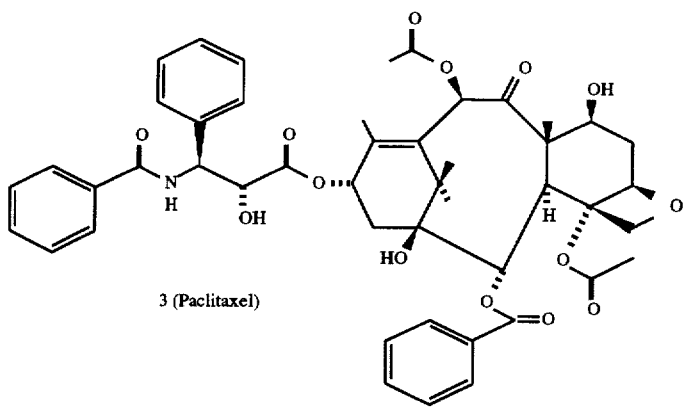

3 (Paclitaxel)

In literature several approaches towards the use and synthesis of prodrugs in ADEPT have been described (reviews: L. N. Jungheim et al. Chem. Rev. 1994, 94, 1553–1566, K. D. Bagshawe, J. Contr. Release 1994, 28, 187–193, K. D. Bagshawe, Clin. Pharmacokinet. 1994, 27, 368–376 and P. M. Wallace and P. D. Senter, Find. Exp. Clin. Pharmacol., 1994, 16, 505–512). Major limitations of the reported prodrugs are a too slow activation by the concomitant enzyme (H. J. Haisma et al. Br. J. Cancer 1992, 66, 474–478, M. Gerken et al. European patent 1991, 0441218A2), prodrug activation by endogenous enzymes (P. D. Senter et al. Cancer Res. 1989, 49, 5789–5792 and Proc. Natl. Acad. Sci. USA 1988, 85, 4842–4846, P. M. Wallace et al. Bioconj. Chem. 1991, 2, 349–352) and a too high cytotoxicity of the prodrug (L. N. Jungheim et al. J. Org. Chem. 1992, 57, 2334–2340).

We developed prodrugs of general formula 1 or 2a,b (vide supra) in which a spacer moiety attached to a sugar group is connected to the 2' hydroxyl functionality of paclitaxel. As a consequence of the importance of the 2' hydroxyl group for the cytotoxic activity of paclitaxel, attachment of a moiety onto this 2' hydroxyl will result in less toxic prodrugs (K. C. Nicolaou et al Angew. Chem. 1994, 106, 38–69). Furthermore, the use of polar sugar groups will give rise to better water soluble paclitaxel prodrugs.

In the spacer part of prodrug 1, $R^1$, $R^2$ and/or $R^3$ are —H or —Me while in the spacer part of prodrug 2a,b n=1 or 2, $R^5$ is —H and/or a group as —Me, $CX_3$ (wherein X is an halogen atom), —Y, —OY, —NHY, —S($O_2$)Y, C(O)Y or C(O)OY (wherein Y=$C_1$–$C_3$ alkyl group or an aryl group). Both in prodrug 1 and in prodrug 2a,b, $R^4$ (sugar part) is —$CH_2OH$ or —C(O)$O^-Z^+$ (wherein $Z^+$ is a proton or an alkali metal ion such as $Li^+$, $Na^+$, $K^+$) which converts to the parent drug paclitaxel (3) upon hydrolysis of the carbohydrate part of the prodrug via the following mechanisms.

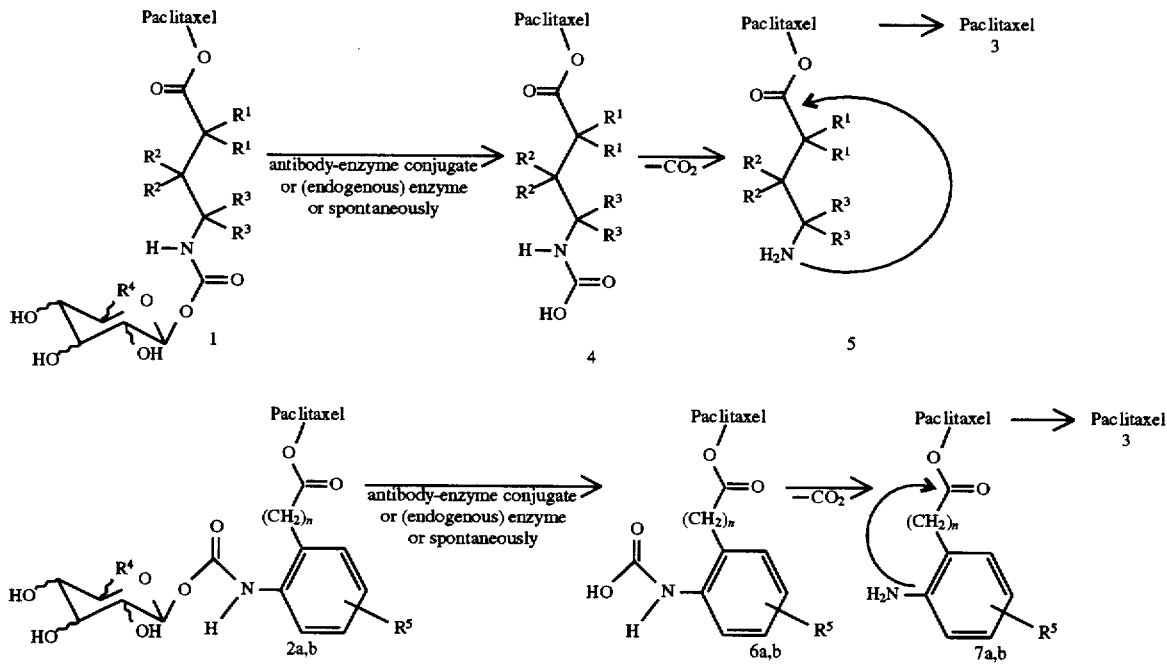

$R^1$, $R^2$, $R^3$ = —H or —$CH_3$; $R^4$ = —$CH_2OH$, —C(O)$O^-Z^+$; $R^5$ = —H, —$CX_3$, —OY, —NHY, —S(O)$_2$Y, —C(O)Y, —C(O)OY

X = halogen; Y = $C_1$–$C_3$ alkyl, aryl; Z = H, Li, Na, K n = 1(a) or 2(b)

mechanism 2

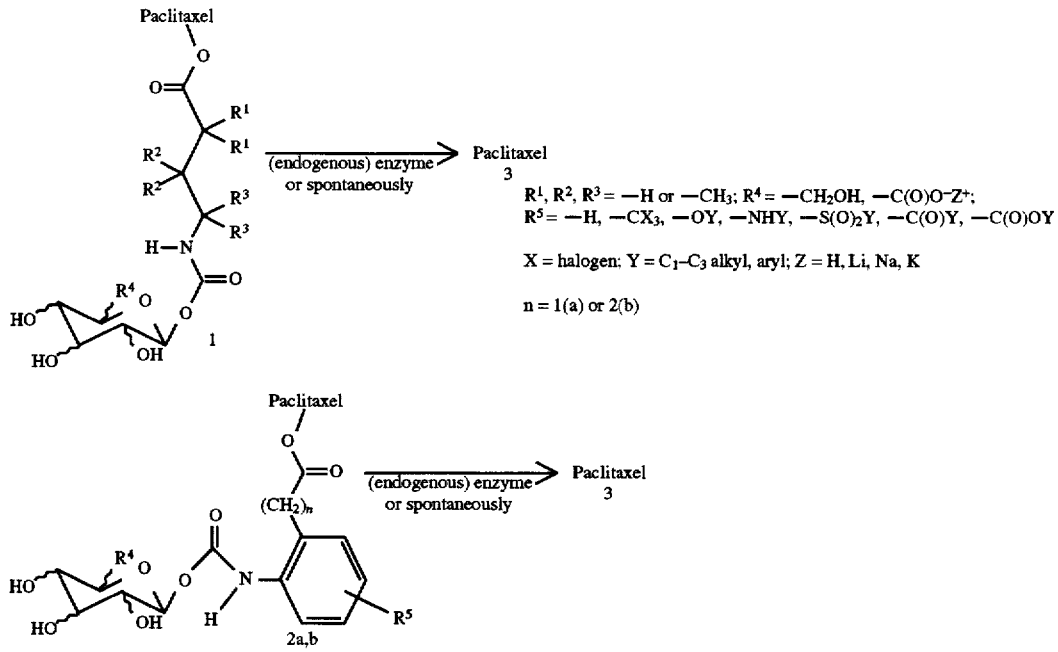

Paclitaxel 3

$R^1$, $R^2$, $R^3$ = —H or —$CH_3$; $R^4$ = —$CH_2OH$, —C(O)O$^-$Z$^+$;
$R^5$ = —H, —$CX_3$, —OY, —NHY, —S(O)$_2$Y, —C(O)Y, —C(O)OY

X = halogen; Y = $C_1$–$C_3$ alkyl, aryl; Z = H, Li, Na, K n = 1(a) or 2(b)

In contrast to prodrugs of paclitaxel as described by H. M. Deutsch et al., *J. Med. Chem.*, 1989, 32, 788–792, R. D. Haugwitz et al., international patent 1989, WO 89/08453, V. J. Stella et al., international patent 1990, WO 90/10433, K. C. Nicolaou et al., *Nature*, 1993, 364, 464–466, D. M. Vyas et al., *Bioorg. and Med. Chem. Lett.*, 1993, 3, 1357–1360. Y. Ueda et al., *Bioorg. and Med. Chem. Lett.*, 1993, 3, 1761–1766. K. C. Nicolaou et al., *Angew. Chemie*, 1994, 105, 1672–1675, Y. Ueda et al., *Bioorg. and Med. Chem. Lett.*, 1994, 4, 1861–1864, R. B. Greenwald et al., *Bioorg. and Med. Chem. Lett.*, 1994, 4, 2465–2470 and R. B. Greenwald et al., *J. Org. Chem.*, 1995, 60, 331–336, M. L. Rodrigues et al., *Chemistry and Biology*, 1995, 2, 223–227, S. W. Mamber et al., *J. Pharm. Exp. Ther.*, 1995, 274, 877–883, in this application the first water-soluble prodrugs of paclitaxel are described with the general formula 1 and 2a,b (vide supra) having a sugar moiety ($R^4$ is —$CH_2OH$ or —C(O)O$^-$Z$^+$ (wherein Z$^+$ is a proton or an alkali metal ion such as Li$^+$, Na$^+$, K$^+$)) attached via a spacer group to paclitaxel. Moreover, the use of a sugar moiety attached via a carbamate linkage to a spacer moiety which, on his counterpart, is connected to paclitaxel allows activation of the prodrug via ADEPT. Using this strategy, paclitaxel can be specifically targeted to tumor cells.

The spacer group can be an aliphatic chain with $R^1$, $R^2$ and/or $R^3$ are —H or —Me or an phenyl group as spacer moiety with $R^5$ is —H and/or a group as —Me, $CX_3$ (wherein X is an halogen atom), —Y, —OY, —NHY, —S(O$_2$)Y, C(O)Y or C(O)OY (wherein Y=$C_1$–$C_3$alkyl group or an aryl group). Removal of the sugar moiety, as a consequence of i.e. antibody-enzyme conjugate hydrolysis, followed by elimination of the spacer moiety by formation of a γ or a δ lactam or hydrolysis as such of the spacer moiety attached to the sugar part liberates the parent drug (i.e. Paclitaxel, see mechanisms 1 and 2, vide supra).

SYNTHESIS

Preparation of the prodrugs 1 and 2a,b starts with the ring opening of anhydride 8 or 16 with allylalcohol resulting in monoesters 9 or 17a, respectively or with the esterfication of diacid 18, also with allylalcohol, yielding 17b.

The key step in the synthesis of prodrugs 1 and 2a,b is the generation of isocyanates 11 and 20a,b at which an anomerically unprotected carbohydrate 12 is attached affording sugar carbamates 13 and 21a,b respectively (R. G. G. Leenders et al. *Tetrahedron Lett.* 1995, 36, 1701–1704). As a result of the desired suicide potential of the spacer, the sugar carbamate moiety can not be introduced via synthetic steps involving intermediates having a free amino group attached to the spacer moiety because of premature ring closure to the corresponding γ or δ lactam, respectively. For this reason we introduced the sugar carbamate fragment in situ, employing the Curtius rearrangement to generate isocyanates as masked carbamates from carboxylic acids 9 and 17a,b. In order to synthesize acylazides 10 and 19a,b, essential for the Curtius rearrangement, from carboxylic esters 9 and 17a,b diphenylphosphoryl azide and triethylamine were added to mono esters 9 and 17a,b. Subsequent heating afforded, after Curtius rearrangement, isocyanates 11 and 20a,b. Reaction of the anomerically unprotected sugar derivative 12 with isocyanates 11 and 20a,b occurred with a high β-selectivity resulting in the protected spacer moieties 13 and 21a,b. Removal of the allyl protective group resulted in acids 14 and 22a,b which were subsequently coupled to paclitaxel (3) affording the fully protected Paclitaxel prodrugs 15 and 23a,b using diisopropylcarbodiimide analogously to R. B. Greenwald et al., *Bioorg. and Med. Chem. Lett.*, 1994, 4, 2465–2470. When dicyclohexylcarbodiimide was used instead of diisopropylcarbodiimide we encountered problems during purification by silicagel chromatography caused by dicyclohexylurea. Hydrogenolysis of the benzyl protective groups using hydrogen and palladium on carbon as a catalyst, followed by ionexchange and purification by LH-20 gelfiltration afforded the paclitaxel prodrugs 1 and 2a,b.
The above described syntheses of prodrugs 1 and 2a,b is illustrated by examples 1, 2 and 3 (vide infra).
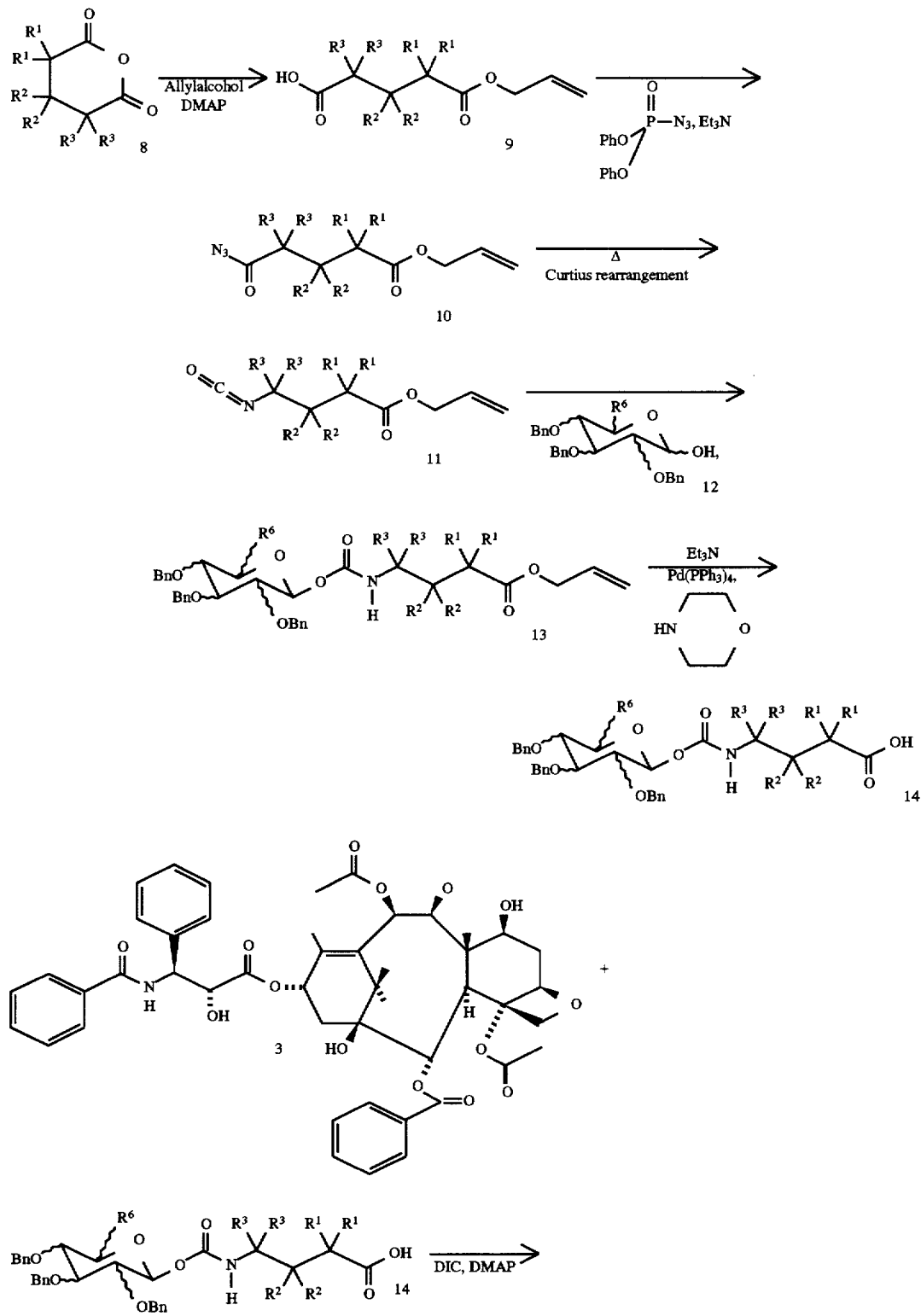

-continued
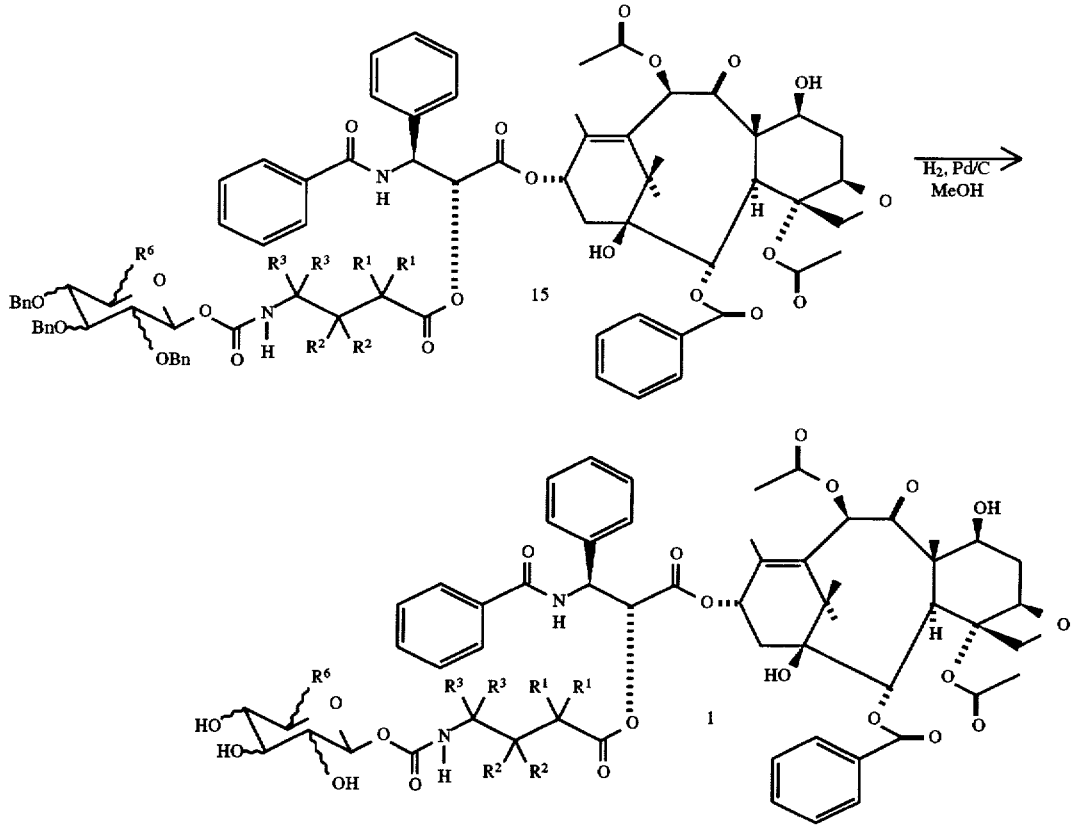
$R^1$, $R^2$, $R^3$ = —H or —CH$_3$; $R^4$ = CH$_2$OH, C(O)O$^-$Z$^+$; $R^6$ = —CH$_2$OBn, —C(O)OBn
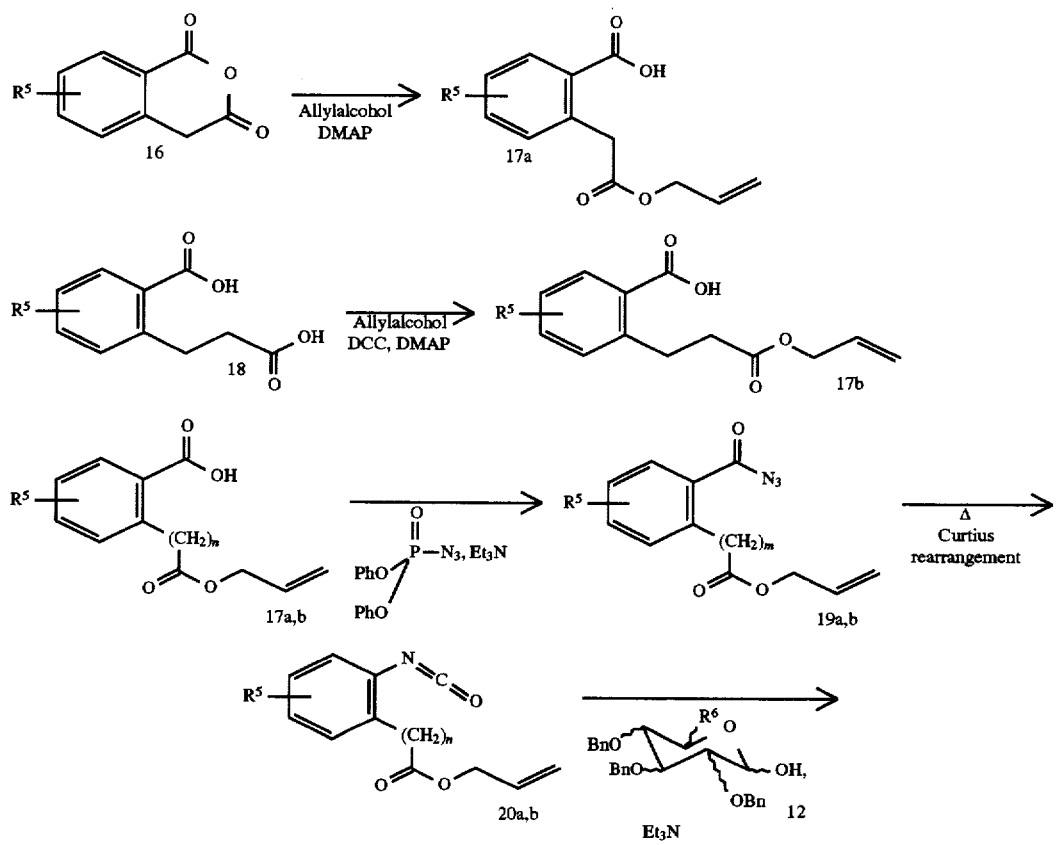

-continued
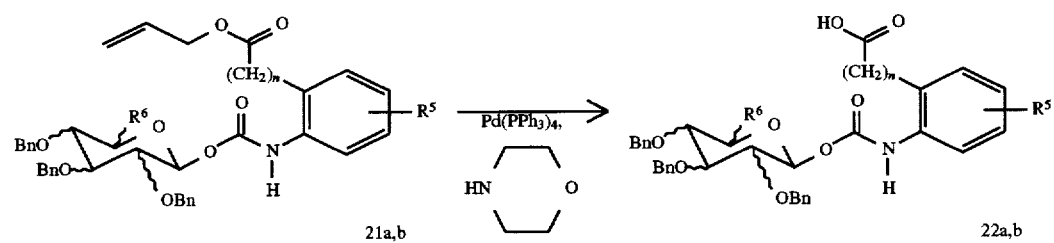
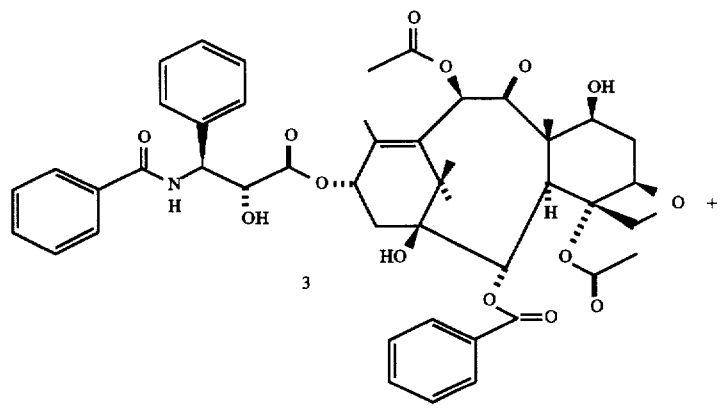
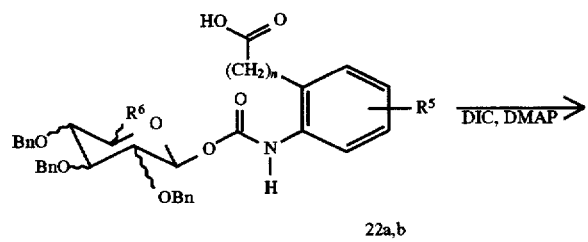
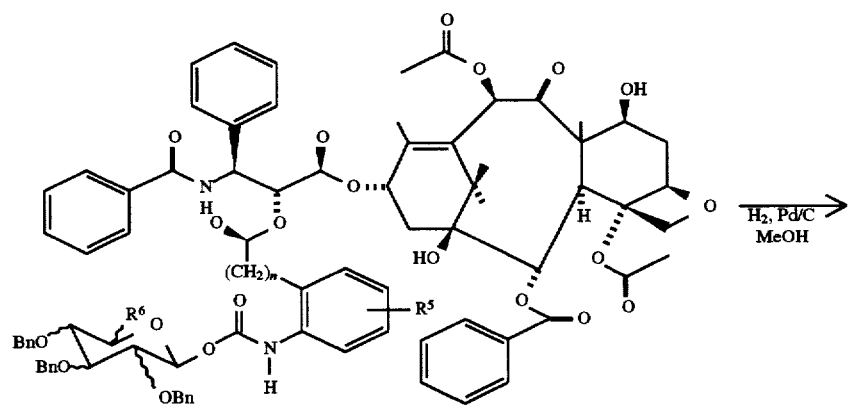

-continued

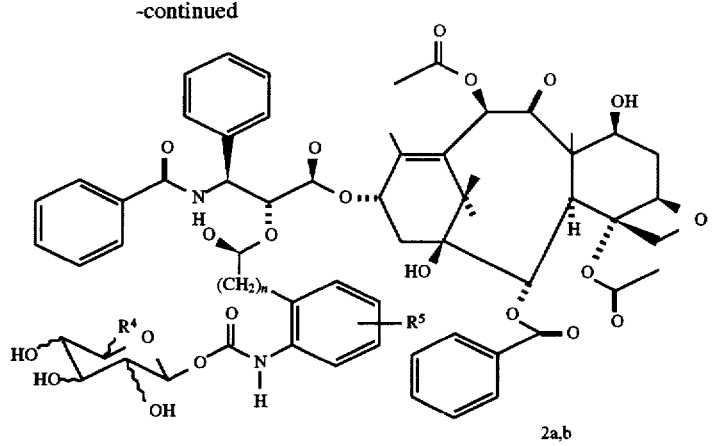

2a,b $R^6$ = —$CH_2OBn$, —$C(O)OBn$; $R^5$ = —H, —$CX_3$, —OY, —NHY, —C(O)Y, —C(O)OY
$R^4$ = $CH_2OH$, $C(O)O^-Z^+$;
Y = $C_1$–$C_3$ alkyl, aryl; n = 1(a) or 2(b)

PHARMACOLOGY

Biological characterization of Paclitaxel prodrugs having general formula 1 or 2a,b consists of
Stability assay
In vitro cytotoxicity assay
Enzyme hydrolysis assay The prodrugs in examples 1 and 2b were all stable in PBS buffer (PBS buffer=NaCl (8 g/L), KCl (0.2 g/L), $Na_2HPO_4$ (1.15 g/L), $KH_2PO_4$ (0.2 g/L), pH=6.8, see example 4 and 5).

The prodrugs 1 and 2a,b, synthesized as described above, were far more better soluble in water as the parent drug paclitaxel. Concentrations of 10 mM in water and higher were reached whereas the solubility of paclitaxel is lower as 0.005 μM in water (K. C. Nicolaou et al., Nature, 1993, 364, 464–466).

Compound 2a was not stable in PBS buffer and decomposed to paclitaxel (3) with a half time of 3 hr (example 6).

Activation of the prodrugs 1 and 2b was possible using the appropriate enzyme (example 7 and 8) with quite fast hydrolyzing rates. During the enzyme catalyzed hydrolysis of prodrugs 1b and 2b to paclitaxel (3) no intermediates, having only the spacer molecule attached to paclitaxel (i.e. compounds 5 and 7b) were detected.

Both prodrugs 1 and 2b were less cytotoxic as the parent drug (example 9).

Prodrug 2a is about as cytotoxic as paclitaxel (example 9) due to spontaneous decomposition of the spacer.

EXAMPLE 1

Paclitaxel glucuronide prodrug with aliphatic spacer, substituted with methyl groups (1)
($R^1$ and $R^3$=H, $R^2$=$CH_3$)
1-allyl-3,3-dimethylglutaric ester (9)

To a solution of 2.1 g 3,3-dimethylglutaric anhydride (14.7 mmol) in allylalcohol (10 mL) was added triethyl amine (2 mL, 14.7 mmol) and a catalytic amount of dimethylaminopyridine (DMAP). After completion of the reaction (3 hr), as was monitored by GC, the reaction mixture was diluted with ethylacetate and washed with an aqueous solution of 1N $KHSO_4$ and brine, respectively, followed by drying over anhydrous $Na_2SO_4$. Evaporation of the solvent afforded 9 ($R^1$ and $R^3$=H, $R^2$=$CH_3$) as an oil in 90% yield (2.6 g).

$^1H$ NMR (100 MHz, ppm, $CDCl_3$): 1.14 (s, 6H, Me (both)), 2.47 (s, 4H, $CH_2$ (both)), 4.60 (dt, 2H, $CH_2$ (allyl), $J_{vic}$=5.6 Hz, $J_{1,4=CH\alpha}$=$J_{1,4=CH\beta}$=1.2 Hz), 5.23 (ddt, 1H, =$CH_\alpha$(allyl), $J_{vic}$=10.1 Hz, $J_{gem}$=1.7 Hz, $J_{1,4}$=1.2 Hz), 5.31 (ddt, 1H, =$CH_\beta$(allyl), $J_{vic}$=17.2 Hz, $J_{gem}$=1.7 Hz, $J_{1,4}$=1.2 Hz), 5.93 (8 lines, 1H, $CH_2$—C$\underline{H}$=$CH_2$, $J_{CH,=CH\beta}$=17.2 Hz, $J_{CH,=CH\alpha}$=10.1 Hz, $J_{CH, CH2}$=5.6 Hz).

Mass spectrometry: 200 ($M^+$, EI).

N-[allyl-3,3-dimethyl butanoate]-O-[2,3,4,6-tetrabenzyl β-glucuronyl] carbamate 13

In dry $CH_2Cl_2$ (10 mL) was dissolved 0.6 g of allyl ester 9 (3 mmol). Subsequently, 0.50 mL triethyl amine (3.6 mmol) and 0.78 mL diphenylphosphorylazide (3.6 mmol) were added and the reaction was stirred. After completion of the reaction, as was monitored by GC, the solvent was evaporated and the residue was subjected to kughelruhr distillation (130° C., 1 mm Hg) resulting in isocyanate 11 after Curtius rearrangement (yield: 487 mg, 83%). Isocyanate 11 was immediately dissolved in dry toluene (10 mL), followed by addition of 0.91 g 1-hydroxy-2,3,4,6-tetrabenzyl glucuronic acid (12) (1.65 mmol) and a few drops triethyl amine as a catalyst. The reaction mixture was heated to 70° C. for one night and subsequently refluxed for another night, the solvent was evaporated under reduced pressure, and the residue was subjected to silica gel chromatography (silica 60 H, eluens 20% ethylacetate in hexanes). Compound 13 was obtained as an oil in a conversion yield of 87% (0.81 g). Further elution afforded 1-hydroxy-2,3,4,6-tetrabenzyl glucuronic acid (12) (0.23 g, 0.41 mmol).

$^{13}C$ NMR (25.4 MHz, ppm, $CDCl_3$): 25.4 and 25.5 ($CH_3$ spacer (both)), 34.6 ($\underline{C}(CH_3)_2$ spacer), 43.8 ($\underline{CH_2}$C=O spacer), 50.4 ($\underline{CH_2}$NH spacer), 65.1, 67.3, 74.9 and 75.7 ($\underline{CH_2}$Ph, 4 times), 74.6, 79.3 and 80.5 ($C^2$, $C^3$ and $C^4$ glucuronic acid) 83.7 ($C^5$glucuronic acid), 94.8 ($C^1$ glucuronic acid), 116.6 (=$CH_2$ allyl), 127.6, 128.8, 127.9, 128.2, 128.3, 128.4 and 131.8 (CH Ph, $CH_2\underline{C}H$=$CH_2$ allyl), 134.8, 137.5, 137.8 and 138.0 (Cq Ph), 154.3 (N$\underline{C}$(O)O), 166.2 and 171.6 ($C^6$glucuronic acid and C(O) spacer).

$^1H$ NMR (400 MHz, ppm, $CDCl_3$): 0.99 and 1.00 (s, 6H, $CH_3$ spacer (both)), 2.20 (d, 1H, $CH_\alpha$C(O) spacer, $J_{gem}$=13.7 Hz), 2.26 (d, 1H, $CH_\beta$C(O) spacer, $J_{gem}$=13.7 Hz), 3.11 (d, 2H, C$\underline{H}_2$NH spacer, $J_{vic}$=6.7 Hz), 3.60 (dd, 1H, $C^2$H glucuronic acid, $J_{2,1}$=$J_{2,3}$=8.2 Hz), 3.73 (dd, 1H, $C^3$H glucuronic acid, $J_{3,2}=J_{3,4}=8.8$ Hz), 3.82 (dd, 1H, C$^4$H glucuronic acid, $J_{4,3}=J_{4,5}=9.9$ Hz), 4.09 (d, 1H, C$^5$H glucuronic acid, $J_{5,4}=9.9$ Hz), 4.42 and 4.85 (both d, both 1H, CH$_\alpha$Ph and CH$_{\beta Ph}$, $J_{gem}=10.6$ Hz (both)), 4.56 (d, 2H, OCH$_2$allyl, $J_{vic}=5.8$ Hz), 4.69 and 4.87 (both d, both 1H, CH$_\alpha$Ph and CH$_\beta$Ph, $J_{gem}=11.2$ Hz (both)), 4.74 (s, 2H, C(O)OCH$_2$Ph), 5.13 and 5.18 (both d, both 1H, CH$_\alpha$Ph and CH$_\beta$Ph, $J_{gem}=12.3$ Hz (both)), 5.22 (t, 1H, NH, $J_{vic}=6.6$ Hz), 5.24 (d, 1H, =CH$_\alpha$, $J_{=CH\alpha,CH}=11.1$ Hz), 5.31 (d, 1H, =CH$_\beta$, $J_{=CH\beta,CH}=17.0$ Hz), 5.62 (d, 1H, C$^1$H glucuronic acid, $J_{vic}=8.2$ Hz), 5.90 (8 lines, 1H, CH$_2$CH=CH$_2$ allyl, $J_{CH,=CH\beta}=17.0$ Hz, $J_{CH,=CH\alpha}=11.1$ Hz, $J_{CH,CH2}=5.9$ Hz), 7.09–7.30 (m, 24H, Ph).

Mass spectrometry (FAB): 752 (M+H)$^+$, 774 (M+Na)$^+$ and 790 (M+K)$^+$.

N-[paclitaxel-2'-O-3,3-dimethylbutanoate]-O-[2,3,4, 6-tetrabenzyl β-glucuronyl] carbamate (15)

0.87 g Allyl ester 13 (0.12 mmol) was dissolved in THF, followed by addition of 46 μL of morpholine (0.58 mmol). After bubbling of argon gas for 15 min. through the solution, a few crystals of palladiumtetrakistriphenylphosphine were added. When the reaction was complete, as was demonstrated by TLC (eluent ethylacetate/hexanes, 1/1, v/v), the mixture was diluted with ethylacetate, washed with 1N KHSO$_4$, dried over anhydrous Na$_2$SO$_4$ and the solvent was evaporated under reduced pressure yielding acid 14 which was not further purified but immediately coupled to paclitaxel (vide infra).

After dissolving acid 14 in CH$_2$Cl$_2$ (5 mL), 50 mg paclitaxel (58 μmol) was added and the mixture was cooled to 0° C. Subsequently, 18 μL diisopropylcarbodiimide (0.12 mmol), a few crystals of dimethylaminopyridine were added and the reaction mixture was stirred at 0° C. for 1 hr. When the reaction was complete, as was monitored by TLC (eluent CH$_2$Cl$_2$/MeOH, 95/5, v/v), the mixture was diluted with CH$_2$Cl$_2$, washed with an aqueous solution of 1N KHSO$_4$, saturated NaHCO$_3$, water, brine and dried over anhydrous Na$_2$SO$_4$. Evaporation of the solvent under reduced pressure, followed by purification over silicagel chromatography (silica 60H, eluens EtOAc/hexanes, 1/1, v/v) afforded the fully protected paclitaxel prodrug 15 in a yield of 79% (71.4 mg) which was pure according to TLC (eluent CH$_2$Cl$_2$/MeOH, 95/5, v/v) and HPLC (C$^{18}$ reverse phase column, eluent: gradient of 10% acetonitrile in water to 90% acetonitrile in water, detection at 226 nm).

$^{13}$C NMR(75.4 MHz, ppm, CDCl$_3$): 9.6 (C$^{19}$ paclitaxel), 14.7 (C$^{18}$ paclitaxel), 20.8 (C$^{10}$OC(O)CH$_3$ paclitaxel), 22.2 (C$^4$OC(O)CH$_3$ paclitaxel), 22.8 (C$^{17}$ paclitaxel), 25.2 and 26.2 (CH$_3$ spacer (both)), 26.8 (C$^{16}$ paclitaxel), 34.7 (Cq spacer), 35.5 (C$^6$ paclitaxel), 35.7 (C$^{14}$ paclitaxel), 42.3 (C$^{15}$ paclitaxel), 43.2 (CH$_2$C(O) spacer), 45.6 (C$^3$ paclitaxel), 49.4 (CH$_2$NH spacer), 52.8 (C$^{3'}$ paclitaxel), 58.5 (C$^8$paclitaxel), 67.3 (CH$_2$Ph), 71.7 (C$^7$ paclitaxel), 72.1 (C$^{13}$paclitaxel), 74.7, 75.2, 75.6 and 80.6 (C$^2$, C$^{10}$ and C$^{2'}$ paclitaxel, C$^2$H, C$^3$H and C$^4$H glucuronic acid), 74.8 and 75.0 (CH$_2$Ph), 79.1 (C$^{20}$paclitaxel), 79.2 (C$^1$ paclitaxel), 81.1 (C$^4$paclitaxel), 83.6 (C$^5$paclitaxel), 84.5 (C$^5$H glucuronic acid), 95.0 (C$^1$H glucuronic acid), 125.5, 126.6, 127.7, 127.7, 127.8, 127.9, 127.9, 128.2, 128.2, 128.3, 128.4, 128.5, 128.6, 128.7, 128.9, 130.2 130.6 and 133.5 (CH Ph), 129.2, 132.7, 134.8, 137.2, 137.6, 138.0 and 138.1 (Cq Ph) 133.9 (C$^{11}$paclitaxel), 142.8 (C$^{12}$paclitaxel), 154.5 (C(O) carbamate), 167.0, 167.6, 168.0, 168.2, 170.0, 170.5 and 171.1 (N$^{3'}$ C(O) paclitaxel, C$^{2'}$OC(O)Ph paclitaxel, C$^{1'}$ paclitaxel, C$^4$OC(O)CH$_3$ paclitaxel, C$^{10}$OC(O)CH$_3$ paclitaxel, C$^6$(O) glucuronic acid, C(O) spacer) and 203.8 (C$^9$ paclitaxel).

$^1$H NMR (500 MHz, ppm, CDCl$_3$): 0.86 (s, 3H, CH$_3$ spacer), 0.94 (s, 3H, CH$_3$ spacer), 1.13 (s, 3H, C$^{17}$H$_3$ paclitaxel), 1.23 (s, 3H, C$^{16}$H$_3$ paclitaxel), 1.69 (s, 3H, C$^{19}$H$_3$ paclitaxel), 1.89 (ddd, 1H, C$^6$H$_\beta$ paclitaxel, $J_{C6H\beta,C5H}=2.8$ Hz, $J_{C6H\beta,C7H}=10.2$ Hz, $J_{C6H\beta,C6H\alpha}=14.4$ Hz), 1.96 (d, 3H, C$^{18}$H$_3$ paclitaxel, $J_{1,4}=0.9$ Hz), 2.04 (d, 1H, C$_\alpha$C(O) spacer, $J_{gem}=13.0$ Hz), 2.12 (dd, 1H, C$^{14}$H$_\beta$ paclitaxel, $J_{gem}=15.4$ Hz, $J_{vic}=9.2$ Hz), 2.23 (s, 3H, C$^{10}$OC(O)CH$_3$ paclitaxel), 2.28 (d, 1H, CH$_\alpha$C(O) spacer, $J_{gem}=13.0$ Hz), 2.44 (dd, 1H, C$^{14}$H$_\alpha$ paclitaxel, $J_{gem}=15.4$ Hz, $J_{vic}=9.2$ Hz), 2.49 (d, 1H, C$^7$OH paclitaxel, $J_{vic}=4.2$ Hz), 2.57 (ddd, 1H, C$^6$H$_\alpha$ paclitaxel, $J_{C6H\alpha,C5H}=8.8$ Hz, $J_{C6H\alpha,C7H}=6.6$ Hz, $J_{C6H\alpha,C6H\beta}=14.4$ Hz), 2.58 (s, 3H, C$^4$OC(O)CH$_3$ paclitaxel), 2.85 (dd, 1H, CH$_\beta$NH spacer, $J_{gem}=14.1$ Hz, $J_{vic}=5.1$ Hz), 3.55 (dd, 1H, C$^2$H glucuronic acid, $J_{C2H,C1H}=J_{C2H,C3H}=7.5$ Hz), 3.56 (dd, 1H, CH$_\alpha$NH spacer, $J_{gem}=14.1$ Hz, $J_{vic}=8.5$ Hz), 3.58 (dd, 1H, C$^3$H glucuronic acid, $J_{C3H,C2H}=J_{C3H,C4H}=8.5$ Hz), 3.65 (d, 1H, C$^5$H glucuronic acid, $J_{C5H,C4H}=9.6$ Hz), 3.78 (dd, 1H, C$^4$H glucuronic acid, $J_{C4H,C3H}=9.1$ Hz), 3.83 (d, 1H, C$^3$H paclitaxel, $J_{vic}=7.1$ Hz), 4.22 (d, 1H, C$^{20}$H$_\beta$ paclitaxel, $J_{gem}=8.4$ Hz), 4.32 (d, 1H, C$^{20}$H$_\alpha$ paclitaxel, $J_{gem}=8.4$ Hz), 4.39 and 4.66 (both d, both 1H, C H$_\alpha$Ph and CH$_\beta$Ph, $J_{gem}=10.9$ Hz (both)), 4.46 (ddd, 1H, C$^7$H, $J_{C7H,C6H\alpha}=6.6$ Hz, $J_{C7H,C6H\beta}=11.2$ Hz, $J_{C7H,OH}=4.2$ Hz), 4.67 and 4.77 (both d, both 1H, CH$_\alpha$Ph and CH$_\beta$Ph, $J_{gem}=11.6$ Hz (both)), 4.71 (dd, 1H, CH$_2$NHspacer, $J_{NH,CH\alpha}=8.5$ Hz, $J_{NH,CH\beta}=5.1$ Hz), 4.77 and 4.82 (both d, both 1H, CH$_\alpha$Ph and CH$_\beta$Ph, $J_{gem}=10.9$ Hz (both)), 4.83 and 4.99 (both d, both 1H, CH$_\alpha$Ph and CH$_\beta$Ph, $J_{gem}=12.1$ Hz (both)), 4.98 (m, 1H, C$^5$H paclitaxel), 5.38 (d, 1H, C$^1$H glucuronic acid, $J_{vic}=7.5$ Hz), 5.50 (d, 1H, C$^{2'}$H paclitaxel, $J_{vic}=3.0$ Hz), 5.86 (d, 1H, C$^2$H paclitaxel, $J_{vic}=7.2$ Hz), 6.08 (dd, 1H, C$^3$H paclitaxel, $J_{C3'H,NH}=9.5$ Hz, $J_{C3'H,C2'H}=3.0$ Hz), 6.30 (s, 1H, C$^{10}$H paclitaxel), 6.31 (dd, 1H, C$^{13}$H paclitaxel, $J_{C13H,C14H\alpha}=J_{C13H,C14H\beta}=9.6$ Hz), 7.05–8.16 (m, 35H, Ph), 7.99 (d, 1H, NH paclitaxel, $J_{vic}=9.5$ Hz).

Mass spectrometry (FAB): 1547 (M+H)$^+$, 1569 (M+Na)$^+$.

Elemental analysis measured C: 67.77%, H: 6.49%, N: 2.40%, calculated (with 1 H$_2$O): C: 67.55%, H: 6.18%, N: 1.79%.

N-[paclitaxel-2'-O-3,3-dimethyl butanoate]-O-[β-glucuronyl] carbamate sodium salt (1)

49.4 mg fully protected prodrug 15 (32 μmol) was dissolved in MeOH (20 mL), transferred to an autoclave, charged under a nitrogen atmosphere and a catalytic amount of palladium on carbon (10%) was added. Subsequently, the reaction mixture was treated with hydrogen gas (50 atm.) and stirred for 24 hr. After completion of the reaction, as was monitored by HPLC (C$^{18}$ reverse phase column, eluent: gradient of 10% acetonitrile in water to 90% acetonitrile in water, detection at 226 nm), the mixture was centrifuged at 5000 rpm for 5 min, the supernatants was decanted followed by evaporation of the solvent under reduced pressure. Dissolving the residue in tert. butanol/H$_2$O (1/1, v/v, 20 mL), addition of Dowex-Na, in order to prepare the sodium salt, lyophilizing the solvent followed by purification using LH-20 gelfiltration (eluent acetonitrile/H$_2$O, 85/15, v/v) afforded compound 1 in a yield of 43% (16.8 mg) which was pure according to HPLC (C$^{18}$ reverse phase column, eluent: gradient of 10% acetonitrile in water to 90% acetonitrile in water, detection at 226 nm).

$^1$H NMR (400 MHz, ppm, DMSO d$_6$, T=305K): 0.92 (s, 3H, CH$_3$ spacer), 0.97 (s, 3H, CH$_3$ spacer), 1.06 (s, 3H, C$^{17}$H$_3$ paclitaxel), 1.09 (s, 3H, C$^{16}$H$_3$ paclitaxel), 1.56 (s, 3H, C$^{19}$H$_3$ paclitaxel), 1.57 (m, 1H, C$^6$H$_b$ paclitaxel), 1.69

(m, 2H, $CH_\alpha C(O)$ spacer and $C^{14}H_\beta$ paclitaxel), 1.84 (s, 3H, $C^{18}H_3$ paclitaxel), 1.89 (dd, 1H, $C^{14}H_\alpha$ paclitaxel, $J_{gem}$= 14.9 Hz, $J_{vic}$=9.1 Hz), 2.16 (s, 3H, $C^{10}OC(O)CH_3$ paclitaxel), 2.35 (m, 5H, $CH_\alpha C(O)$ spacer, $C^4OC(O)CH_3$ paclitaxel and $C^6H_\alpha$ paclitaxel), 2.49 (d, 1H, $C^7OH$ paclitaxel, $J_{vic}$=4.2 Hz), 2.96 (dd, 1H, $CH_\beta NH$ spacer, $J_{gem}$= 13.5 Hz, $J_{vic}$=5.9 Hz), 3.03 (dd, 1H, $CH_\alpha NH$ spacer, $J_{gem}$= 13.5 Hz, $J_{vic}$=6.5 Hz), 3.18 (m, 1H, $C^2H$ glucuronic acid), 3.66 (d, 1H, $C^3H$ paclitaxel, $J_{vic}$=7.2 Hz), 4.06 (d, 1H, $C^{20}H_\beta$ paclitaxel, $J_{gem}$=8.2 Hz), 4.10 (d, 1H, $C^{20}H_\alpha$ paclitaxel, $J_{gem}$=8.2 Hz), 4.19 (ddd, 1H, $C^7H$, $J_{C7H,C6H\alpha}$=6.9 Hz, $J_{C7H,C6H\beta}$=10.4 Hz, $J_{C7H,OH}$=6.5 Hz), 4.64 (s, 1H, $C^1OH$ paclitaxel), 4.93 (d, 1H, $C^7OH$, paclitaxel), 4.97 (d, 1H, $C^5H$ paclitaxel, $J_{C5H,C6H\alpha}$=10.6), 5.12 (bs, 1H, $C^2OH$ glucuronic acid), 5.16 (d, 1H, $C^5H$ glucuronic acid, $J_{C5H,C4H}$=5.3 Hz) .5.30 (d, 1H, $C^1H$ glucuronic acid, $J_{vic}$=7.6 Hz), 5.44 (d, 1H, $C^2H$ paclitaxel, $J_{vic}$=8.8 Hz), 5.47 (d, 1H, $C^2H$ paclitaxel, $J_{vic}$=7.0 Hz), 5.62 (dd, 1H, $C^3H$ paclitaxel, $J_{C3'H,NH}$=$J_{C3'H,C2'H}$=8.2 Hz), 5.87 (dd, 1H, $C^{13}H$ paclitaxel, $J_{C13H,C14H\alpha}$=$J_{C13H,C14H\beta}$=9.1 Hz), 6.36 (s, 1H, $C^{10}H$ paclitaxel), 7.16–7.98 (m, 15H, Ph), 9.17 (d, 1H, NH paclitaxel, $J_{vic}$=8.2 Hz).

Mass spectrometry (FAB): 1209 (M+H)$^+$, 1231 (M+Na)$^+$.

EXAMPLE 2

Paclitaxel glucuronide prodrug with aromatic spacer (2a) ($R^5$=H, n=1)

allyl-(2-carboxylic acid)phenylacetate (17a)

17a was prepared as described for the synthesis of 9 using 3.25 g homophtalic anhydride (16) (20 mmol), 10 mL allyl alcohol, 3.1 mL triethyl amine (22 mmol) and a few crystals DMAP. After completion of the reaction, work-up was carried out as described for 9 (vide supra). Evaporation of the solvent and purification by crystallization from hexanes afforded allyl ester 17a in 83% (3.65 g) which was pure according to GC.

$^1$H NMR (100 MHz, ppm, CDCl$_3$): 3.88 (s, 2H, PhC$H_2$C(O)), (ddd, 2H, OCH$_2$allyl, $J_{vic}$=5.6 Hz, $J_{CH2,=CH\alpha}$=$J_{CH2,=CH\beta}$=1.3 Hz), 4.95 (ddt, 1H, =CH$_\alpha$, $J_{vic}$=17.2 Hz, $J_{1,4}$=$J_{gem}$=1.3 Hz), 4.98 (ddt, 1H, =CH$_\beta$, $J_{vic}$=10.2 Hz, $J_{1,4}$=$J_{gem}$=1.3 Hz), 5.72 (ddt, 1H, CH$_2$CH=CH$_2$ allyl, $J_{CH,CH2}$=5.6 Hz, $J_{CH,=CH\alpha}$=17.2, $J_{CH,=CH\beta}$=10.2), 7.03–7.42 (m, 3H, CH Ph), 7.92 (dd, 1H, $C^3H$ Ph, $J_{vic}$=7.60, $J_{1,4}$=1.8 Hz), 12.0 (s, 1H, C(O)OH).

$^{13}$C NMR (25.4 MHz, ppm): 40.8 (CH$_2$C(O)), 85.6 (OCH$_2$ allyl), 116.4 (=CH$_2$ allyl), 127.9, 132.0, 132.2, 132.6 and 133.4 (CH Ph and CH$_2$CH=CH$_2$allyl), 128.7 ($C^1$ Ph), 138.8 ($C^2$ Ph), 171.3 and 172.8 (C(O) both).

Mass spectrometry (EI): 220 (M$^+$) and 1251 (M+Na)$^+$.

Elemental analysis: Calculated for C$_{12}$H$_{12}$O$_4$: C 56.45, H 5.49, measured: C 65.40, H 5.39.

N-[(2-allylacetate)phenyl]-O-[2,3,4,6-tetrabenzyl β-glucuronyl] carbamate 21a

To a solution of 220 mg allylester 17a (1 mmol) in dry toluene (5 mL) was added 0.17 mL triethyl amine (1.2 mmol) and 0.26 mL diphenylphosphorylazide (1.2 mmol). Stirring for 1 night, upon which azide 19a was formed, followed by heating of the reaction mixture for 2 hr at 65° C. resulted in isocyanate 20a which was not isolated but directly converted to carbamate 21a by addition of 0.28 g glucuronic acid derivative 12 (0.5 mmol) to the reaction mixture containing isocyanate 20a. After completion of the addition of glucuronic acid derivative 12 to isocyanate 20a (2 days), which was monitored by TLC (eluent ethylacetate/hexanes, 1/1, v/v), the reaction mixture was diluted with ethylacetate, washed with an aqueous solution of 1N KHSO$_4$, an aqueous solution of saturated NaHCO$_3$, brine and water and dried over anhydrous Na$_2$SO$_4$. Purification by silicagel chromatography (silica 60H, eluent ethylacetate/hexanes, 1/3, v/v) afforded 21a as a white solid (yield 82%, 315 mg) which was pure according to TLC.

$^1$H NMR (400 MHz, ppm, CDCl$_3$): 3.54 and 3.66 (both d, both 1H, C(O)C$H_\alpha$Ph and C(O)C$H_\beta$Ph spacer, $J_{gem}$=14.7 Hz (both)), 3.69 (m, 1H, CH glucuronic acid), 3.77 (dd, 1H, CH glucuronic acid, $J_{vic}$=8.8 Hz), 3.87 (dd, 1H, CH glucuronic acid, $J_{vic}$=9.1 Hz), 4.14 (d, 1H, $C^5H$ glucuronic acid, $J_{vic}$= 10.0 Hz), 4.44 and 4.70 (both d, both 1H, CH$_\alpha$Ph and CH$_\beta$Ph, $J_{gem}$=10.6 Hz (both)), 4.58 (d, 2H, OCH$_2$ allyl, $J_{vic}$=5.9 Hz), 4.80 (d, 1H, CH$_\alpha$Ph $J_{gem}$=10.6 Hz), 4.81 (m, 3H, CH$_\beta$Ph (two times) and NH), 4.88 (d, 1H, CH$_\alpha$Ph $J_{gem}$=11.2 Hz), 5.14 and 5.18 (both d, both 1H, CH$_\alpha$Ph and CH$_\beta$Ph, $J_{gem}$=12.3 Hz (both)), 5.23 (d, 1H, =CH$_\alpha$, $J_{=CH\alpha,CH}$=10.6 Hz), 5.27 (d, 1H, =CH$_\beta$, $J_{=CH\beta,CH}$=17.2 Hz), 5.72 (d, 1H, $C^1H$ glucuronic acid, $J_{vic}$=7.6 Hz), 5.87 (8 lines, 1H, CH$_2$CH=CH$_2$ allyl, $J_{CH,=CH\beta}$=17.2 Hz, $J_{CH,=CH\alpha}$=10.6 Hz, $J_{CH,CH2}$=5.9 Hz), 7.09–8.22 (m, 24H, Ph).

$^{13}$C NMR (25.4 MHz, ppm, CDCl$_3$): 38.4 (CH$_2$C(O) spacer), 66.1, 67.4, 74.9 and 75.7 (CH$_2$Ph), 79.3, 80.4 and 83.9 ($C^2H$, $C^3H$, $C^4H$ and $C^5H$ glucuronic acid), 95.1 ($C^1H$ glucuronic acid), 118.9 (=CH$_2$ allyl), 125.1, 127.7, 127.8, 128.2, 128.3, 128.4, 128.5, 130.7 and 131.3 (CH$_2$CH=CH$_2$, CH Ph), 134.8, 136.0, 137.5, 137.8 and 138.0 (Cq Ph), 151.8 (C(O) carbamate), 166.2 and 171.8 (C$^1$(O) glucuronic acid and C(O) spacer).

Mass spectrometry (FAB): 794 (M+Na)$^+$.

Elemental analysis: measured: C 71.43, H 5.98 and N 1.83, calculated for C$_{46}$H$_{45}$O$_{10}$N: C 71.58, H 5.88 and N 1.81

N-[paclitaxel-2'-O-(2-amino)phenylacetate]-O-[2,3,4,6-tetrabenzyl β-glucuronyl] carbamate (23a)

In THF (5 mL) was dissolved 0.18 g allyl ester 21a (0.23 mmol). Subsequently, 100 μL morpholine (1.2 mmol) was added, argon gas was bubbled through the solution for 15 min followed by addition of a few crystals of palladiumtetrakistriphenylphosphine. After completion of the reaction, as was demonstrated by TLC (eluent ethylacetate/hexanes, 1/1, v/v), the mixture was diluted with ethylacetate, washed with an aqueous solution of 1H KHSO$_4$, dried over anhydrous Na$_2$SO$_4$ and the solvent evaporated under reduced pressure yielding carboxylic acid 22a which was not further purified.

The above prepared acid 22a and 50 mg paclitaxel (58 μmol) were dissolved in dry CH$_2$Cl$_2$ (5 mL). After cooling this solution to 0° C., 18 μL diisopropylcarbodiimide (0.12 mmol) and a few crystals dimethylaminopyridine were added. As was monitored by TLC (eluent CH$_2$Cl$_2$/MeOH, 95/5, v/v), the reaction was complete after 1 hr. The reaction mixture was subsequently diluted with CH$_2$Cl$_2$, washed with an aqueous solution of 1N KHSO$_4$, saturated NaHCO$_3$, water, brine and dried over anhydrous Na$_2$SO$_4$. Evaporation of the solvent under reduced pressure, followed by purification over silicagel chromatography (silica 60H, eluens EtOAc/hexanes, 1/1, v/v) afforded the fully protected paclitaxel prodrug 23a in a quantitative yield (96 mg) which was pure according to TLC (eluent CH$_2$Cl$_2$/MeOH, 95/5, v/v) and HPLC (C$^{18}$ reverse phase column, eluent: gradient of 10% acetonitrile in water to 90% acetonitrile in water, detection at 226 nm).

$^{13}$C NMR (100 MHz, ppm, CDCl$_3$) 10.5 (C$^{19}$ paclitaxel), 15.1 (C$^{18}$ paclitaxel), 20.9 (C$^{10}$OC(O)$\underline{C}$H$_3$ paclitaxel), 22.4 (C$^4$OC(O)$\underline{C}$H$_3$ paclitaxel), 23.4 (C$^{17}$ paclitaxel), 27.1 (C$^{16}$ paclitaxel), 36.5 (C$^6$ paclitaxel), 37.4 (C$^{14}$ paclitaxel), 37.8 (CH$_2$spacer), 44.5 (C$^{15}$ paclitaxel), 47.9 (C$^3$ paclitaxel), 55.1 (C$^{3'}$ paclitaxel), 59.2 (C$^8$paclitaxel), 68.5 ($\underline{C}$H$_2$Ph), 72.3 (C$^7$ paclitaxel), 73.0 (C$^{13}$ paclitaxel), 75.7, 75.9 and 76.4 (C$^2$, C$^{10}$, C$^{20}$ and C$^{2'}$ paclitaxel, $\underline{C}$H$_2$Ph and CH glucuronic acid), 79.0 (C$^1$paclitaxel), 80.4 (CH glucuronic acid), 82.2 (C$^4$ paclitaxel), 82.3 (CH glucuronic acid), 84.4 (C$^5$paclitaxel), 85.9 (CH glucuronic acid), 96.7 (C$^1$H glucuronic acid), 127.9, 128.5, 128.7, 128.9, 129.4, 129.6, 129.7, 130.0, 131.2, 131.4, 132.0, 134.6, 134.8, 135.2, 136.6, 136.7, 138.3 139.2 and 139.7 (CH and Cq Ph), 133.0 (C$^{11}$ paclitaxel), 142.4 (C$^{12}$paclitaxel), 155.1 (C(O) carbamate), 159.9 (N$^3$C (O)), 167.7 (C$^2$O$\underline{C}$(O)Ph), 170.1, 170.2, 171.3, 171.6 and 171.9 (C$^{1'}$, C$^4$O$\underline{C}$(O)CH$_3$, C$^{10}$O$\underline{C}$(O)CH$_3$paclitaxel, C$^6$(O) glucuronic acid, C(O) spacer) and 205.2 (C$^9$ paclitaxel).

$^1$H NMR (500 MHz, ppm): 1.09 (s, 6H, C$^{17}$H$_3$ and C$^{16}$H$_3$ paclitaxel), 1.68 (s, 3H, C$^{19}$H$_3$ paclitaxel), 1.89 (ddd, 1H, C$^6$H$_\beta$, J$_{C6H\beta,C5H}$=2.6 Hz, J$_{C6H\alpha,C7H}$=11.4 Hz, J$_{C6H\alpha,C6H\beta}$=14.5 Hz), 1.91 (s, 3H, C$^{18}$H$_3$ paclitaxel), 2.05 (bs, 1H, C$^{14}$H$_\beta$ paclitaxel), 2.21 (s, 3H, C$^{10}$OC(O)CH$_3$ paclitaxel), 2.35 (bs, 1H, C$^{14}$H$_\beta$ paclitaxel), 2.47 (bs, 3H, C$^4$OC(O)CH$_3$ paclitaxel), 2.49 (d, 1H, C$^7$OH, J$_{vic}$=4.0 Hz), 2.55 (ddd, 1H, C$^6$H$_\beta$, J$_{C6H\beta,C5H}$=9.3 Hz, J$_{C6H\beta,C7H}$=6.3 Hz, J$_{C6H\beta,C6H\alpha}$=14.5 Hz), 3.63–3.80 (m, 6H, OC(O)CH$_2$Ph spacer, C$^3$ paclitaxel, C$^2$H C$^3$H and C$^4$H glucuronic acid), 4.10 (bs, 1H, C$^5$H glucuronic acid), 4.20 (d, 1H, C$^{20}$H$_\beta$ paclitaxel, J$_{gem}$=8.5 Hz), 4.31 (d, 1H, C$^{20}$H$_\alpha$ paclitaxel, J$_{gem}$=8.5 Hz), 4.42 and 4.68 (both d, both 1H, CH$_\alpha$Ph and CH$_\beta$Ph, J$_{gem}$=10.8 Hz (both)), 4.44 (m, 1H, C$^7$H paclitaxel), 4.76 and 4.82 (both d, both 1H, CH$_\alpha$Ph and CH$_\beta$Ph, J$_{gem}$=11.0 Hz (both)), 4.67–4.78 (m, 2H, C$\underline{H}_2$Ph), 4.96 (d, 1H, C$^5$H paclitaxel J$_{C5H,C6H\alpha}$=9.4 Hz), 5.12 (m, 2H, C$\underline{H}_2$Ph), 5.43 (bs, 1H, C$^{2'}$H paclitaxel), 5.66 (m, 2H, C$^{2'}$H paclitaxel and C$^1$H glucuronic acid), 5.92 (bs, 1H, C$^3$H paclitaxel), 6.26 (s, 1H, C$^{10}$H paclitaxel), 6.23 (m, 1H, C$^{13}$H paclitaxel), 6.62 (bs, 1H, NH paclitaxel) 7.09–8.16 (m, 35H, Ph paclitaxel).

Mass spectrometry (FAB): 1589 (M+Na)$^+$.

N-[paclitaxel-2'-O-(2-amino) phenylacetate]-O-[β-glucuronyl] carbamate sodium salt (2a)

In methanol (20 mL) was dissolved 58.7 mg of compound 23a (37 μmol). Subsequently, the solution was transferred to an autoclave, brought under a nitrogen atmosphere, a catalytic amount of palladium on carbon (10%) was added and the reaction mixture was treated with hydrogen gas (50 atm.). After 1 day the hydrogenolysis was complete as was shown by HPLC (C$^{18}$ reverse phase column, eluent: gradient of 10% acetonitrile in water to 90% acetonitrile in water, detection at 226 nm). Centrifugation (5000 rpm, 5 min.) and decantation followed by evaporation under reduced pressure of the solvent resulted in a solid which was resolved in tert. butanol/H$_2$O (1/1, v/v, 20 mL). Subsequent ion exchange using Dowex-Na, lyophilizing of the solvent and purification by gelfiltration (LH-20, eluent acetonitrile/H$_2$O, 85/15, v/v) afforded prodrug 2a in a yield of 33% (15.2 mg) which was pure according to HPLC (C$^{18}$ reverse phase column, eluent: gradient of 10% acetonitrile in water to 90% acetonitrile in water, detection at 226 nm).

Mass spectrometry (FAB): 1229 (M+H)$^+$ and 1251 (M+Na)$^+$.

$^1$H NMR data of 2a:

$^1$H NMR (400 MHz, ppm, DMSO δ$_6$, T=298K): 0.99 (s, 3H, C$^{17}$H$_3$ paclitaxel]9, 1.01 (s, 3H, C$^{16}$H$_3$ paclitaxel), 1.47 (s, 3H, C$^{19}$H$_3$ paclitaxel), 1.49 (m, 1H, C$^{14}$H$_\beta$ paclitaxel), 1.60 (m, 1H, C$^6$H$_\beta$ paclitaxel), 1.75 (s, 3H, C$^{18}$H$_3$ paclitaxel), 1.81 (dd, 1H, C$^{14}$H$_\alpha$ paclitaxel), J$_{gem}$=15.2 Hz, J$_{vic}$=9.7 Hz), 2.09 (s, 3H, C$^{10}$OC(O)CH$_3$ paclitaxel), 2.23 (s, 3H C$^4$OC(O)CH$_3$ paclitaxel), 2.30 )m, 1H, C$^6$H$_\alpha$ paclitaxel), 3.56 (d, 1H, C$^3$H paclitaxel, J$_{vic}$=8.2 Hz), 3.79 (d, 1H, C$^{20}$H$_\beta$ paclitaxel, J$_{gem}$=16.3 Hz), 3.86 (d, 1H, C$^{20}$H$_\alpha$ paclitaxel, J$_{gem}$=16.3 Hz), 3.99 (s, 2H, CH$_2$ spacer), 4.09 (m, 1H, C$^7$H), 4.60 (s, 1H, C$^1$OH paclitaxel), 4.89 (d, 1H, C$^5$H paclitaxel, J$_{gem}$=10.3), 4.92 (m, 1H, C$^7$O$\underline{H}$ paclitaxel), 5.12 (bs, 1H, C$^2$OH, paclitaxel), 5.22 (d, 1H, C$^1$H glucuronic acid, J$_{vic}$=5.2 Hz), 5.33 (d, 1H, C$^{2'}$H paclitaxel, J$_{vic}$=8.2 Hz), 5.40 (d, 2H, C$^2$H paclitaxel and C$^5$H glucuronic acid, J$_{vic}$=8.7 Hz), 5.54 (dd, 1H, C$^{3'}$H paclitaxel, J$_{C3'H,NH}$=J$_{C3'H,C2'H}$=8.2 Hz), 5.82 (m, 1H, C$^{13}$H paclitaxel), 6.27 (s, 1H, C$^{10}$H paclitaxel), 6.91–7.98 (m, 19H, Ph).

EXAMPLE 3

Paclitaxel glucuronide prodrug with aromatic spacer (2b) (R$^5$=H, n=2)

allyl-3-(2-carboxyphenyl) propionate (17b)

194 mg 3-(2-carboxyphenyl)propionic acid (18) (1 mmol) and 75 μL allylalcohol (1.1 mmol) were dissolved in a mixture of dry CH$_2$Cl$_2$ (5 mL) and dry DMF (0.5 mL). After cooling of the solution to 0° C., 206 mg dicyclohexylcarbodiimide (1 mmol) and a few crystals of dimethylaminopyridine were added, the reaction mixture was stirred at 0° C. for 4 hr and another 12 hr at room temperature. Work-up was carried out as follows: the reaction mixture was filtrated, the filtrate diluted with CH$_2$Cl$_2$, washed with an aqueous solution of 1N KHSO$_4$, dried over anhydrous Na$_2$SO$_4$ and the solvent was evaporated under reduced pressure. Redissolving the obtained ester in hexanes, followed by filtration in order to remove traces of dicyclohexylurea and evaporation of the solvent under reduced pressure afforded 17b as an oil (91%, 212 mg).

$^1$H NMR (100 MHz, ppm): 3.30 (t, 2H, C$\underline{H}_2$Ph spacer, J$_{vic}$=7.7 Hz), 3.93 (t, 2H, C$\underline{H}_2$C(O) spacer, J$_{vic}$=7.7 Hz), 5.14 (dt, 2H, OCH$_2$ allyl, J$_{vic}$=5.6 Hz, J$_{1,4}$=1.2 Hz), 5.77 (10 lines, 1H, =CH$_\alpha$, J$_{vic}$=10.1 Hz, J$_{gem}$=1.2 Hz, J$_{1,4}$=1.2 Hz), 5.86 (10 lines, 1H, =CH$_\beta$, J$_{vic}$=17.1 Hz, J$_{gem}$=1.2 Hz, J$_{1,4}$=1.2 Hz), 6.46 (12 lines, CH$_2$C$\underline{H}$=CH$_2$, J$_{CH,CH\beta}$=17.1 Hz, J$_{CH,CH\alpha}$=10.1 Hz, J$_{CH,CH2}$=5.5 Hz), 7.79–8.12 (m, 3H, CH Ph), 8.64 (1H, dd, C$^3$H Ph, J$_{vic}$=11.8 Hz, J$_{1,4}$=2.0 Hz) and 9.34 (s, 1H, C(O)OH).

$^{13}$C NMR (25.4 MHz, ppm): 30.1 (Ph$\underline{C}$H$_2$), 35.8 ($\underline{C}$H$_2$C(O)), 65.3 (OCH$_2$ allyl), 118.2 (=CH$_2$ allyl), 126.8 (CH allyl), 128.4 (C$^1$ Ph), 131.6, 132.1, 132.3 and 133.3 (C$^3$, C$^4$, C$^4$ and C$^6$ Ph), 143.5 (C$^2$ Ph), 172.8 and 172.9 (C(O) both).

Mass spectrometry (EI): 234 (M$^+$).

N-[(2-allylpropionate)phenyl]-O-[2,3,4,6-tetrabenzyl β-glucuronyl] carbamate 21b 234 mg of acid 17b (1 mmol) was dissolved in 5 mL of dry toluene whereupon 0.17 mL triethylamine (1.2 mmol) and 0.27 mL diphenylphosphorylazide (1.2 mmol) were added. After stirring for a night, the mixture was heated to 65° C. in order to provoke the Curtius rearrangement giving isocyanate 20b, which was not isolated. Allowing the reaction mixture to cool to room temperature, subsequent addition of 240 mg of glucuronic acid derivative 12 (0.43 mmol), stirring for 48 hr followed by work-up as described for the synthesis of 21a (vide supra) resulted in carbamate 21b, which was further purified by silica gel chromatography (silica 60H, eluent ethylacetate/hexanes, 1/4, v/v). Yield 76% (257 mg) which was pure according to TLC.

$^{13}$C NMR (25.4 MHz, ppm): 25.1 (Ph$\underline{C}$H$_2$CH$_2$C(O) spacer), 35.3 (PhCH$_2$$\underline{C}$H$_2$C(O) spacer), 65.8 (O$\underline{C}$H$_2$ allyl), 67.5, 75.0 and 75.9 ($\underline{C}$H$_2$Ph), 79.5, 80.5 and 83.8 (C$^2$, C$^3$, C$^4$ and C$^5$ glucuronic acid), 95.3 (C$^1$ glucuronic acid), 116.9 (=CH$_2$ allyl), 125.3, 127.4, 127.7, 127.9, 128.2, 128.4, 128.5, 128.8, 128.9, 129.7 and 131.7 (CH Ph and CH$_2$$\underline{C}$H=CH$_2$ allyl), 132.1, 135.0, 135.2, 137.7, 138.0 and 138.3 (Cq Ph), 152.1 (C(O) carbamate), 166.5 and 174.0 (C$^6$ glucuronic acid and C(O) spacer).

$^1$H NMR (400 MHz, ppm, CDCl$_3$, T=325K): 2.67 (m, 2H, PhC$\underline{H}_2$CH$_2$C(O) spacer), 2.85 9 m, 2H, PhCH$_2$C$\underline{H}_2$C(O) spacer), 3.69 (dd, 1H, C$^2$H glucuronic acid, J$_{C2H,C3H}$=J$_{C2H,C1H}$=8.2 Hz), 3.75 (dd, 1H, C$^3$H glucuronic acid, J$_{C3H,C4H}$=J$_{C3H,C2H}$=8.8 Hz), 3.88 (dd, 1H, C$^4$H glucuronic acid, J$_{C4H,C5H}$=J$_{C4H,C3H}$=9.4 Hz), 4.14 (d, 1H, C$^5$H glucuronic acid, J$_{vic}$=9.4 Hz), 4.46 and 4.69 (both d, both 1H, CH$_\alpha$Ph and CH$_\beta$Ph, J$_{gem}$=10.6 Hz (both)), 4.48 (d, 2H, OCH$_2$ allyl, J$_{vic}$=5.9 Hz), 4.76 and 4.83 (both d, both 1H, CH$_\alpha$Ph and CH$_\beta$Ph, J$_{gem}$=11.7 Hz), 4.77 and 4.86 (both d, both H, CH$_\alpha$Ph and CH$_\beta$Ph, J$_{gem}$=11.2 Hz), 5.13 and 5.17 (both d, both 1H, CH$_\alpha$Ph and CH$_\beta$Ph, J$_{gem}$=12.0 Hz), 5.15 (d, 1H, =CH$_\alpha$, J$_{=CH\alpha,CH}$=10.6 Hz), 5.19 (d, 1H, =CH$_\beta$, J$_{=CH\beta,CH}$=17.0 Hz), 5.73 (d, 1H, C$^1$H glucuronic acid, J$_{vic}$=7.6 Hz), 5.79 (8 lines, 1H, CH$_2$C$\underline{H}$=CH$_2$ allyl, J$_{CH,=CH\beta}$=17.0 Hz, J$_{CH,=CH\alpha}$=10.6 Hz, J$_{CH,CH2}$=5.9 Hz), 7.07–7.84 (m, 25H, Ph and NH).

Mass spectrometry (FAB): 808 (M+Na)$^+$.

Elemental analysis: measured: C 71.14%, H 5.97% and N 1.91%, calculated for C$_{47}$H$_{47}$O$_{10}$N: C 71.83%, H 6.03% and N 1.91%

N-[paclitaxel-2'-O-(2-amino)phenylpropionate]-O-[2,3,4,6-tetrabenzyl β-glucuronyl] carbamate (23b)

To a solution of 135 mg allyl ester 21b (0.17 mmol) was added 67 μL morpholine (0.86 mmol) whereupon argon gas was bubbled through the mixture during 15 min. Subsequently, a few crystals of palladiumtetrakistriphenylphosphine were added and the reaction mixture was stirred for 1 hr. After completion of the reaction, as was monitored by TLC (eluent ethylacetate/hexanes, 1/1, v/v), work-up was carried out as follows: the reaction mixture was diluted with ethylacetate, washed with an aqueous solution of 1N KHSO$_4$, dried over anhydrous Na$_2$SO$_4$ and the solvent was evaporated under reduced pressure. The thus obtained acid 22b was not further purified but directly solved in dry CH$_2$Cl$_2$ (5 mL). To this solution was added 50 mg paclitaxel (58 μmol) and the mixture was cooled to 0° C. Subsequently, 18 μL diisopropylcarbodiimide (0.12 mmol) and a few crystals of dimethylaminopyridine were added.

After completion of the reaction, as was demonstrated by TLC (eluent CH$_2$Cl$_2$/MeOH, 95/5, v/v), the reaction mixture was diluted with CH$_2$Cl$_2$, washed with an aqueous solution of 1N KHSO$_4$, an aqueous solution of saturated NaHCO$_3$, H$_2$O, respectively, dried over anhydrous Na$_2$SO$_4$ and the solvent was evaporated under reduced pressure. Purification by chromatography (silica gel 60H, eluent ethylacetate/ hexanes, 46/54, v/v) afforded 23b which was pure according to TLC and HPLC. Yield 83% (75.7 mg).

$^{13}$C NMR (75.5 MHz, ppm, CDCl$_3$) 9.6 (C$^{19}$ paclitaxel), 14.6 (C$^{18}$ paclitaxel), 20.7 (C$^{10}$OC(O)$\underline{C}$H$_3$ paclitaxel), 22.0 (C$^4$OC(O)$\underline{C}$H$_3$ paclitaxel), 22.6 (C$^{17}$ paclitaxel), 25.0 (Ph $\underline{C}$H$_2$CH$_2$C(O) spacer), 26.8 (C$^{16}$ paclitaxel), 29.6 (PhCH$_2$ $\underline{C}$H$_2$C(O) spacer), 34.1 (C$^6$ paclitaxel), 35.6 (C$^{14}$ paclitaxel), 43.1 (C$^{15}$ paclitaxel), 45.6 (C$^3$ paclitaxel), 52.8 (C$^{3'}$ paclitaxel), 58.5 (C$^8$paclitaxel), 67.5, 74.9, 75.4 and 76.4 ($\underline{C}$H$_2$Ph), 71.9 (C$^7$ paclitaxel), 72.0 (C$^{13}$ paclitaxel), 74.2, 74.8, 75.1, 75.5 and 80.3 (C$^2$, C$^{10}$ and C$^{2'}$ paclitaxel, C$^2$H, C$^3$H and C$^4$H glucuronic acid), 79.1 (C$^{20}$ paclitaxel), 79.3 (C$^1$paclitaxel), 81.0 (C$^4$paclitaxel), 83.7 (C$^5$paclitaxel), 84.4 (C$^5$H glucuronic acid), 95.1 (C$^1$H glucuronic acid), 126.5, 127.0, 127.4, 127.7, 127.8, 127.9, 128.0, 128.3, 128.4, 128.5, 128.6, 128.7, 128.8, 129.0, 130.2 and 131.9 (CH Ph), 132.9, 133.6, 134.6, 134.8, 136.7, 137.6, 137.9 and 138.8 (Cq Ph), 133.6 (C$^{11}$paclitaxel), 142.4 (C$^{12}$paclitaxel), 151.4 (C(O) carbamate), 167.0, 167.1, 167.9, 168.4, 169.8, 171.0 and 172.7 (N$^{3'}$C(O), C$^2$O$\underline{C}$(O)Ph, C$^{1'}$(O), C$^4$O$\underline{C}$(O)CH$_3$, C$^{10}$O$\underline{C}$(O)CH$_3$paclitaxel, C$^6$(O) glucuronic acid and C(O) spacer) and 203.7 (C$^9$ paclitaxel).

$^1$H NMR (500 MHz, ppm): 1.13 (s, 3H, C$^{17}$H$_3$ paclitaxel), 1.21 (s, 3H, C$^{16}$H$_3$ paclitaxel), 1.68 (s, 3H, C$^{19}$H$_3$ paclitaxel), 1.87 (ddd, 1H, C$^6$H$_\alpha$, J$_{C6H\alpha,C5H}$=2.4 Hz, J$_{C6H\alpha,C7H}$=9.1 Hz, J$_{C6H\alpha,C6H\beta}$=14.0 Hz), 1.87 (d, 3H, C$^{18}$H$_3$ paclitaxel, J$_{1,4}$=1.2 Hz), 2.12 (dd, 1H, C$^{14}$H$_\beta$ paclitaxel, J$_{gem}$=15.4 Hz, J$_{vic}$=8.9 Hz), 2.20 (s, 3H, C$^{10}$OC(O)CH$_3$ paclitaxel), 2.33 (dd, 1H, C$^{14}$H$_\beta$ paclitaxel, J$_{gem}$=15.4 Hz, J$_{vic}$=8.9 Hz), 2.39 (s, 3H, C$^4$OC(O)CH$_3$paclitaxel), 2.55 (d, 1H, C$^7$OH, J$_{vic}$=4.2 Hz), 2.56 (ddd, 1H, C$^6$H$_\beta$, J$_{C6H\beta,C5H}$=9.7 Hz, J$_{C6H\beta,C7H}$=6.7 Hz, J$_{C6H\beta,C6H\alpha}$=14.0 Hz), 2.81 (m, 4H, PhC$\underline{H}_2$C$\underline{H}_2$C(O) spacer), 3.66 (m, 1H, C$^2$H glucuronic acid), 3.75 (dd, 1H, C$^3$H glucuronic acid, J$_{C3H,C2H}$=J$_{C3H,C4H}$=8.5 Hz), 3.79 (d, 1H, C$^3$ paclitaxel, J$_{vic}$=7.1 Hz), 3.84 (dd, 1H, C$^4$H glucuronic acid, J$_{C4H,C3H}$=J$_{C4H,C5H}$=8.5 Hz), 4.10 (d, 1H, C$^5$H glucuronic acid, J$_{C5H,C4H}$=8.5 Hz), 4.19 (d, 1H, C$^{20}$H$_\beta$ paclitaxel, J$_{gem}$=8.4 Hz), 4.31 (d, 1H, C$^{20}$H$_\alpha$ paclitaxel, J$_{gem}$=8.4 Hz), 4.39 and 4.66 (both d, both 1H, CH$_\alpha$Ph and CH$_\beta$Ph, J$_{gem}$=10.9 Hz (both)), 4.44 (m, 1H, C$^7$H paclitaxel), 4.43 and 4.69 (both d, both 1H, CH$_\alpha$Ph and CH$_\beta$Ph, J$_{gem}$=10.9 Hz (both)), 4.78–4.86 (m, 4H, C$\underline{H}_2$Ph), 4.96 (dd, 1H, C$^5$H paclitaxel J$_{C5H,C6H\alpha}$=9.6 Hz, J$_{C5H,C6H\beta}$=2.0 Hz), 5.12 (m, 2H, C$\underline{H}_2$Ph), 5.52 (d, 1H, C$^{2'}$H paclitaxel, J$_{vic}$=3.7 Hz), 5.67 (d, 1H, C$^2$H paclitaxel, J$_{vic}$=7.1 Hz), 5.69 (d, 1H, C$^1$H glucuronic acid, J$_{vic}$=8.0 Hz), 5.94 (bs, 1H, C$^3$H paclitaxel), 6.28 (s, 1H, C$^{10}$H paclitaxel), 6.21 (dd, 1H, C$^{13}$H paclitaxel, J$_{C13H,C14H\alpha}$=J$_{C13H,C14H\beta}$=8.9 Hz), 7.09–8.14 (m, 35H, Ph and NH paclitaxel).

Mass spectrometry (FAB): 1603 (M+Na)$^+$

N-[paclitaxel-2'-O-(2-amino)phenylpropionate]-O-[β-glucuronyl] carbamate sodium salt (2b)

39.3 mg of compound 23b (25 μmol) was dissolved in methanol (20 mL)). Subsequently, the solution was transferred to an autoclave, brought under a nitrogen atmosphere, a catalytic amount of palladium on carbon (10%) was added and the reaction mixture was treated with hydrogen gas (50 atm.). As was demonstrated HPLC (C$^{18}$ reverse phase column, eluent: gradient of 10% acetonitrile in water to 90% acetonitrile in water, detection at 226 nm) the hydrogenolysis was complete after 24 hr. Subsequent centrifugation (5000 rpm, 5 min.) and decantation followed by evaporation under reduced pressure of the solvent resulted in a solid which was resolved in tert. butanol/H$_2$O (1/1, v/v, 20 mL). Ion exchange using Dowex-Na, lyophilizing of the solvent and purification by gelfiltration (LH-20, eluent acetonitrile/ H$_2$O, 85/15, v/v) afforded prodrug 2a in a yield of 76% (23.6 mg) which was pure according to HPLC (C$^{18}$ reverse phase column, eluent: gradient of 10% acetonitrile in water to 90% acetonitrile in water, detection at 226 nm).

Mass spectrometry (FAB): 1243 (M+H)$^+$ and 1265 (M+Na)$^+$.

$^1$H NMR data of 2b $^1$H NMR (400 MHz, ppm, DMSO $\delta_6$, T=298K): 0.99 (s, 3H, C$^{17}$H$_3$ paclitaxel), 1.01 (s, 3H, C$^{16}$H$_3$ paclitaxel), 1.46 (m, 1H, C$^{14}$H$_\beta$ paclitaxel), 1.48 (s, 3H, C$^{19}$H$_3$ paclitaxel), 1.61 (m, 1H, C$^6$H$_\beta$ paclitaxel), 1.78 (m, 1H, C$^{14}$H$_\alpha$ paclitaxel), 1.80 (s, 3H, X$^{18}$H$_3$ paclitaxel), 2.10 (s, 3H, C$^{10}$OCO(O)CH$_3$ paclitaxel), 2.22 (s, 3H, C$^4$OC(O)CH$_3$ paclitaxel), 2.31 (m, 1H, C$^6$H$_\alpha$ paclitaxel), 2.65–2.95 (m, 4H, CH$_2$spacer, both), 3.57 (d, 1H, C$^3$H paclitaxel, J$_{vic}$=7.0 Hz), 3.99 (2, 2H, C$^{20}$H$_\beta$ and C$^{20}$H$_\alpha$ paclitaxel), 4.11 (m, 1H, C$^7$H), 4.59 (s, 1H, C$^1$OC paclitaxel), 4.90 (d, 1H, C$^5$H, paclitaxel, =10.0), 4.93 (m, 1H, C$^7$OH paclitaxel), 5.09 (bs, 1H, C$^2$OH), 5.21 (d, 1H, C$^1$H glucuronic acid, J$_{vic}$=4.7 Hz), 5.33 (d, 1H, C$^2$H paclitaxel, J$_{vic}$=7.6 Hz), 5.40 (m, 3H, C$^2$H paclitaxel, C$^5$H glucuronic acid and OH), 5.47 (dd, 1H, C$^3$H paclitaxel, J$_{C3'H,NH}$=J$_{C3'H,C2'H}$=8.7 Hz), 5.79 (dd, 1H, C$^{13}$H paclitaxel, J$_{C13H,C14H\alpha}$=J$_{C13H,C14H\beta}$=8.9 Hz), 6.29 (s, 1H, C$^{10}$H paclitaxel), 7.04–7.98 (m, 19H, Ph).

PHARMACOLOGY

EXAMPLE 4

Stability of prodrug 1 (R$^1$ and R$^3$=H, R$^2$=CH$_3$, R$^4$=C(O)O$^-$Na$^+$) in PBS buffer 0.28 mg of prodrug 1 (0.23 μmol) was dissolved in 2.3 mL PBS buffer (NaCl (8 g/L), KCl (0.2 g/L), Na$_2$HPO$_4$ (1.15 g/L), KH$_2$PO$_4$ (0.2 g/L, pH=6.8) and placed in a water bath of 37° C. for 48 hr. Subsequent analysis of the mixture by means of HPLC (C$^{18}$ reverse phase column, eluent: gradient of 10% acetonitrile in water to 90% acetonitrile in water, detection at 226 nm) showed a ratio of prodrug 1/paclitaxel of 92/8, respectively. The ratio is based on peak areas.

EXAMPLE 5

Stability of prodrug 2b (R$^4$=C(O)O$^-$Na$^+$, R$^5$=H, n=2) in PBS buffer

To 3.0 mL PBS buffer, pH=6.8, was added 0.37 mg of prodrug 2b (0.30 μmol). The mixture was placed in a water bath of 37° C. Analysis of the solution after 48 hr at 37° C. by means of HPLC (C$^{18}$ reverse phase column, eluent: gradient of 10% acetonitrile in water to 90% acetonitrile in water, detection at 226 nm) displayed a ratio of prodrug 2b/paclitaxel of 92/8, respectively. Analysis of the mixture after 66 hr showed a ratio of prodrug 2b/paclitaxel of 89/11, respectively. The ratios are based on peak areas.

EXAMPLE 6

Hydrolysis of prodrug 2a (R$^4$=C(O)O$^-$Na$^+$, R$^5$=H, n=1) in PBS buffer

In 1.1 mL PBS buffer, pH=6.8, was dissolved 0.13 mg of prodrug 2a (0.11 μmol) and placed in a water bath of 37° C. HPLC analysis (C$^{18}$ reverse phase column, eluent: gradient of 10% acetonitrile in water to 90% acetonitrile in water, detection at 226 nm) of the mixture showed a ratio of prodrug 2a/paclitaxel of 55/45, respectively after 3 hr and a ratio of prodrug 2a/paclitaxel of 1/99, respectively after 22 hr. The ratios are based on peak areas.

EXAMPLE 7

Enzyme catalyzed hydrolysis of prodrug 1 (R$^1$ and R$^3$=H, R$^2$=CH$_3$, R$^4$=C(O)O$^-$Na$^+$)

To 140 μL PBS buffer (pH=6.8) was added 20 μL of a 1 mM solution of prodrug 1 in PBS buffer (pH=6.8) and 20 μL of 1% bovine serum albumin also in PBS buffer (pH=6.8). After incubation of the mixture for 10 min. at 37° C. 20 μL of a solution of 0.1 mg mL$^{-1}$ human β-glucuronidase (H. J. Haisma, Hybridoma, in press) was added. Directly after the addition of the enzyme to the reaction mixture an aliquot of 10 μL was taken and diluted with 90 μL cold acetonitrile (−20° C.) in order to stop the enzyme reaction. The reaction mixture was incubated for 3 hr at 37° C. and samples were taken at 15, 30, 45, 60, 90, 120 and 180 min. All samples were quenched by dilution with cold acetonitrile (−20° C.). To demonstrate that the hydrolysis was enzyme mediated a second experiment was carried out as described above in which instead of 20 μL of a solution of 0.1 mg mL$^{-1}$ human β-glucuronidase 20 μL PBS buffer (pH=6.8) was added. In the later experiment also samples of 10 μL were taken at 0, 15, 30, 45, 60, 90, 120 and 180 min and were also diluted with cold acetonitrile (−20° C.). The samples of both experiments were analyzed by HPLC (C$^{18}$ reverse phase column, eluent: gradient of 10% acetonitrile in water to 90% acetonitrile in water, detection at 226 nm). The ratio of prodrug 1 to paclitaxel as shown in table 1 is determined by measuring the peak areas of the appropriate signals. In the experiment without human β-glucuronidase, no paclitaxel was found within the time course of the experiment demonstrating that the hydrolysis found was caused by the enzyme. All experiments were carried out in duplo.

TABLE 1

| T (min) | ratio prodrug 1/placlitaxel |
|---|---|
| 0 | 99/1 |
| 15 | 95/5 |
| 30 | 93/7 |
| 45 | 87/13 |
| 60 | 78/22 |
| 90 | 61/39 |
| 120 | 43/57 |
| 180 | 33/67 |

From the above described experiment, summarized in table 1, it can be concluded that the hydrolysis of prodrug 1 is caused by the enzyme β-glucuronidase with a half life of about 2 hr at a prodrug concentration of 100 μM and an enzyme concentration of 10 μg mL$^{-1}$.

EXAMPLE 8

Enzyme catalyzed hydrolysis of prodrug 2b (R$^4$=C(O)O$^-$Na$^+$, R$^5$=H, n=2)

20 μL of 1 mM solution of prodrug 2b in PBS buffer (pH=6.8) and 20 μL 1% bovine serum albumin also in PBS buffer (pH=6.8) was added to 140 μL PBS buffer (pH=6.8). Subsequently, the mixture was incubated for 10 min. at 37° C. whereafter 20 μL of a solution of 0.1 mg mL$^{-1}$ human β-glucuronidase (H. J. Haisma, Hybridoma, in press) was added and the reaction mixture was incubated at 37° C. Samples were taken and quenched at 0, 15, 30, 45, 60, 90, 120 and 180 min as described above for the enzyme assay of prodrug 1. In order to determine that the hydrolysis was caused by β-glucuronidase, another experiment was carried out without addition of β-glucuronidase as described above in example 7. The samples were analyzed as described for example 7 (vide supra). The results of the HPLC analysis of the samples is shown in table 2. The ratios presented in table 2, are based on peak areas of the appropriate signals. In the experiment without human β-glucuronidase, no paclitaxel was found within the time course of the experiment demonstrating that the hydrolysis found was caused by the enzyme. All experiment were carried out in duplo.

TABLE 2

| T (min) | ratio prodrug 2b/ratio placlitaxel |
|---|---|
| 0 | 99/1 |
| 15 | 87/13 |
| 30 | 74/26 |
| 45 | 55/45 |
| 60 | 41/59 |
| 90 | 24/76 |
| 120 | 20/80 |
| 180 | 15/85 |

From the above described experiment, summarized in table 1, it can be concluded that the hydrolysis of prodrug 2b is caused by the enzyme β-glucuronidase with a half life of about 45 min at a prodrug concentration of 100 μM and an enzyme concentration of 10 μg mL$^{-1}$.

EXAMPLE 9

Cytotoxicity of prodrugs 1 ($R^1$ and $R^3$=H, $R^2$=$CH_3$, $R^4$= C(O)O$^-$Na$^+$), 2a ($R^4$=C(O)O$^-$Na$^+$, $R^5$=H, n=1) and 2b ($R^4$= C(O)O$^-$Na$^+$, $R^5$=H, n=2) with or without β-glucuronidase The anti-proliferative effects of paclitaxel, and the prodrugs 1, 2a and 2b on OVCAR-3 cells were determined by measuring the cell growth with a protein dye stain (H. J. Haisma et al. Cell Biophysics 1994, 24/25, 185–192). Cells were seeded in 96-well tissue culture plates (5000 cells/well) and 24 h later (pro)drugs 1, 2a, 2b or 3 were added with or without excess human β-glucuronidase. After 72 hours the cells were fixed with 25% trichloroacetic acid, stained with 0.4% sulforhodamine B, washed with 1% acetic acid and air-dried. The bound dye was then solubilized with 10 mM Tris and the absorbance read at 492 nm. The antiproliferative effects were expressed as IC$_{50}$ values, which are the (pro) drug concentrations that gave 50% growth inhibition when compared to control cell growth.

TABLE 3

| | | Activation with β-glucuronidase: | | |
|---|---|---|---|---|
| compound | IC$_{50}$ | IC$_{50}$ with β-glucuronidase | ratio IC$_{50}$ prodrug/ IC$_{50}$ paclitaxel | ratio IC$_{50}$ activated prodrug with β-glucuronidase/IC$_{50}$ paclitaxel |
| 1 | 1.9 ± 0.9 10$^{-8}$ | 6.0 ± 3.0 10$^{-10}$ 10$^{-10}$ | 90 | 3 |
| 2a | 2.3 10$^{-10}$ | 2.3 10$^{-10}$ | 1 | 1 |
| 2b | 2.7 ± 0.3 10$^{-8}$ | 1.1 ± 0.6 10$^{-9}$ | 122 | 5 |
| paclitaxel | 2.2 ± 2.0 10$^{-10}$ | | | |

What is claimed is:

1. An anti-tumor composition for administration orally, topically or by injection, containing as active ingredient a paclitaxel prodrug, consisting of paclitaxel coupled to a cleavable N-(aliphatic or aromatic)-O-glycosyl carbamate spacer group, said prodrug having formula 1 or 2a,b

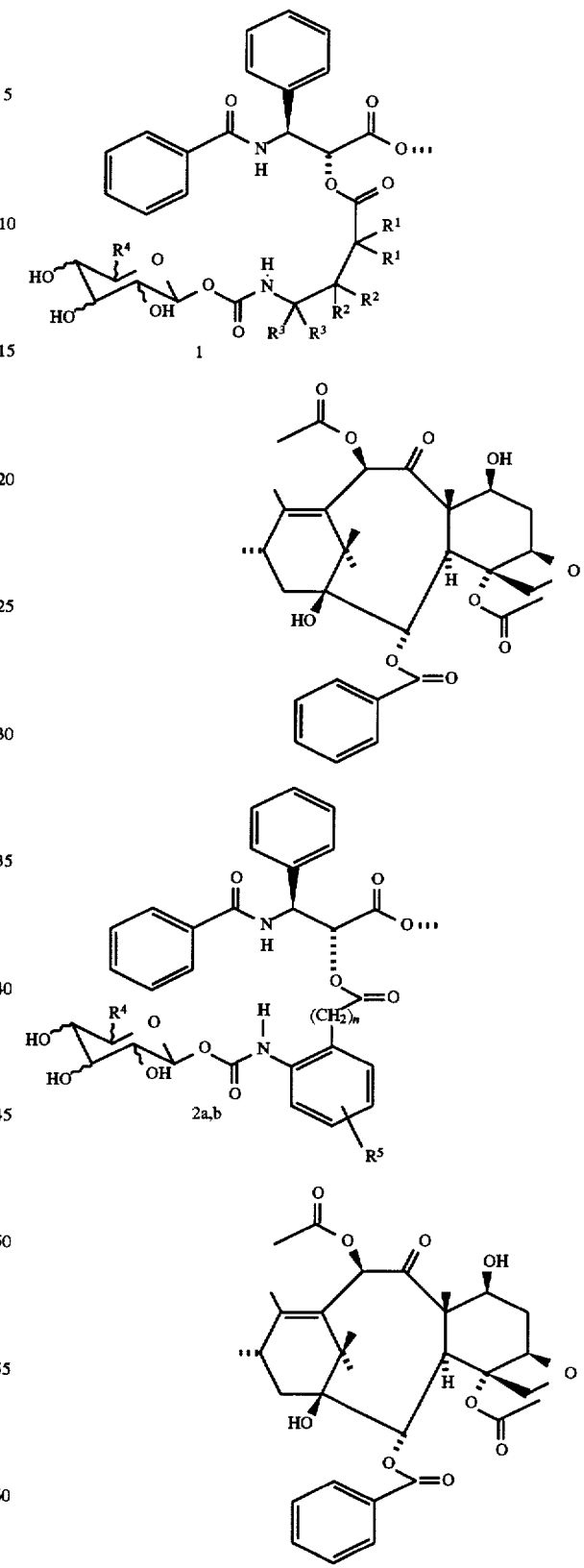

wherein $R^1$, $R^2$, $R^3$=—H or —$CH_3$
$R^4$=—$CH_2OH$, —C(O)O$^-$Z$^+$ $R^5$=—H, —$CX_3$, —OY, —NHY, —$S(O)_2Y$, —C(O)Y, —C(O)OY X=halogen Y=$C_1$-$C_3$ alkyl, aryl Z=H, Li, Na, K n=1(a) or 2(b), or an acid addition salt thereof.

2. A composition according to claim 1, wherein said paclitaxel prodrug is activated by an endogeneous enzyme.

3. A composition according to claim 1, wherein said paclitaxel prodrug is activated by an exogeneous enzyme.

4. A composition according to claim 1, wherein the enzyme is selected from the group consisting of β-glucuronidase, β-glucosidase and β-galactosidase.

5. A method for the treatment of tumors comprising administering an antibody directed enzyme prodrug to a patient in need of said therapy, wherein an antibody targets an enzyme to a tumor site, the improvement wherein said antibody directed enzyme prodrug is a paclitaxel compound of formula 1 or 2a,b according to claim 1, wherein said prodrug passes to the tumor site and said prodrug is rapidly converted at the tumor site by enzymatic hydrolysis directly to a cytotoxic compound, said compound of formula 1 or 2a,b being administered in an amount sufficient to be converted at said tumor site to an anti-tumor effective amount of said cytotoxic compound.

\* \* \* \* \*